US009585780B2

(12) United States Patent
Pacetti

(10) Patent No.: US 9,585,780 B2
(45) Date of Patent: Mar. 7, 2017

(54) PRESSURE CHAMBER AND APPARATUS FOR LOADING MATERIAL INTO A STENT STRUT

(75) Inventor: Stephen D. Pacetti, San Jose, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 1633 days.

(21) Appl. No.: 13/035,811

(22) Filed: Feb. 25, 2011

(65) Prior Publication Data

US 2012/0216916 A1 Aug. 30, 2012

(51) Int. Cl.
*B65B 61/00* (2006.01)
*A61F 2/915* (2013.01)
*B05C 7/00* (2006.01)

(52) U.S. Cl.
CPC .... *A61F 2/915* (2013.01); *A61F 2002/91575* (2013.01); *A61F 2230/0054* (2013.01); *A61F 2250/0068* (2013.01); *B05C 7/00* (2013.01)

(58) Field of Classification Search
None
See application file for complete search history.

(56) References Cited

U.S. PATENT DOCUMENTS

| | | | |
|---|---|---|---|
| 4,459,252 A | 7/1984 | MacGregor | |
| 4,987,854 A * | 1/1991 | Hall | B05B 12/08 118/300 |
| 5,059,211 A | 10/1991 | Stack et al. | |
| 5,163,952 A | 11/1992 | Froix | |
| 5,209,028 A * | 5/1993 | McDermott | B08B 7/0092 134/7 |
| 5,306,286 A | 4/1994 | Stack et al. | |
| 5,527,337 A | 6/1996 | Stack et al. | |
| 5,700,286 A | 12/1997 | Tartaglia et al. | |
| 5,713,949 A | 2/1998 | Jayaraman | |
| 5,766,710 A | 6/1998 | Turnland et al. | |
| 5,769,883 A | 6/1998 | Buscemi et al. | |
| 5,843,172 A | 12/1998 | Yan | |
| 5,873,904 A | 2/1999 | Ragheb et al. | |
| 5,902,266 A | 5/1999 | Leone et al. | |
| 5,972,027 A | 10/1999 | Johnson | |
| 6,120,536 A | 9/2000 | Ding et al. | |
| 6,120,847 A | 9/2000 | Yang et al. | |

(Continued)

FOREIGN PATENT DOCUMENTS

| | | |
|---|---|---|
| EP | 0 850 651 | 1/1998 |
| EP | 0 875 218 | 4/1998 |

(Continued)

OTHER PUBLICATIONS

"Medtronic non-polymeric DES development: from nanoporous coatings to drug filled tubes", Medtronic presentation, 32 pgs (2010).

(Continued)

*Primary Examiner* — Charles Capozzi
(74) *Attorney, Agent, or Firm* — Squire Patton Boggs (US) LLP

(57) ABSTRACT

An apparatus for loading material into a stent strut can comprise a chamber in which a pressure gradient is formed when gas moves through the pressure chamber. While injecting material into a lumen within the stent strut, the pressure gradient inhibits material from leaking out of side holes to the lumen.

15 Claims, 8 Drawing Sheets

(56) References Cited

U.S. PATENT DOCUMENTS

| | | | |
|---|---|---|---|
| 6,206,915 B1 | 3/2001 | Fagan et al. | |
| 6,287,628 B1 | 9/2001 | Hossainy et al. | |
| 6,379,381 B1 | 4/2002 | Hossainy et al. | |
| 6,478,776 B1 | 11/2002 | Rosenman et al. | |
| 6,497,916 B1 | 12/2002 | Taylor et al. | |
| 6,623,519 B2 | 9/2003 | Edwin et al. | |
| 7,335,391 B1* | 2/2008 | Pacetti | A61L 31/10 427/2.1 |
| 7,901,726 B2 | 3/2011 | McMorrow et al. | |
| 2003/0003221 A1* | 1/2003 | Zhong | A61L 31/10 427/2.1 |
| 2004/0009229 A1 | 1/2004 | Unger et al. | |
| 2004/0086542 A1 | 5/2004 | Hossainy et al. | |
| 2004/0133270 A1 | 7/2004 | Grandt | |
| 2005/0182390 A1 | 8/2005 | Shanley | |
| 2005/0263070 A1* | 12/2005 | Fink | H01J 37/32623 118/715 |
| 2005/0288774 A1* | 12/2005 | Case | A61L 27/34 623/1.44 |
| 2007/0043423 A1 | 2/2007 | Grewe | |
| 2007/0110891 A1 | 5/2007 | Pacetti | |
| 2007/0116856 A1 | 5/2007 | Hossainy | |
| 2007/0141232 A1* | 6/2007 | Tochterman | B05B 13/02 427/2.25 |
| 2007/0173923 A1 | 7/2007 | Savage et al. | |
| 2007/0258903 A1 | 11/2007 | Kleiner et al. | |
| 2007/0259101 A1 | 11/2007 | Hossainy et al. | |
| 2008/0188836 A1 | 8/2008 | Weber et al. | |
| 2008/0254086 A1 | 10/2008 | Brown et al. | |
| 2008/0255659 A1 | 10/2008 | Huang et al. | |
| 2009/0098186 A1* | 4/2009 | Kirkpatrick | B05B 5/08 424/424 |
| 2009/0132031 A1 | 5/2009 | Cook et al. | |
| 2009/0287300 A1 | 11/2009 | Dave et al. | |
| 2009/0319032 A1 | 12/2009 | Weber et al. | |
| 2010/0015333 A1* | 1/2010 | McMorrow | B05D 1/02 427/248.1 |
| 2011/0070357 A1 | 3/2011 | Mitchell et al. | |
| 2012/0070563 A1 | 3/2012 | Mitchell et al. | |
| 2012/0165922 A1 | 6/2012 | Gong et al. | |
| 2012/0216905 A1 | 8/2012 | Pacetti | |
| 2012/0216907 A1 | 8/2012 | Pacetti | |
| 2012/0216908 A1 | 8/2012 | Pacetti | |
| 2012/0216912 A1 | 8/2012 | Pacetti | |
| 2012/0216913 A1 | 8/2012 | Pacetti | |
| 2012/0216914 A1 | 8/2012 | Pacetti | |
| 2012/0216916 A1 | 8/2012 | Pacetti | |
| 2013/0276412 A1 | 10/2013 | Pacetti | |
| 2014/0238535 A1 | 8/2014 | Pacetti | |
| 2014/0246120 A1 | 9/2014 | Pacetti | |

FOREIGN PATENT DOCUMENTS

| | | |
|---|---|---|
| JP | 11-299901 | 11/1999 |
| WO | WO 90/01969 | 3/1990 |
| WO | WO 98/23228 | 6/1998 |
| WO | WO 99/16386 | 4/1999 |
| WO | WO 2007-021749 | 2/2007 |
| WO | WO 2008/098926 | 8/2008 |
| WO | WO 2008/098927 | 8/2008 |
| WO | WO 2011/126708 | 10/2011 |

OTHER PUBLICATIONS

Liggins et al., "Solid-State Characterization of paclitaxel", J. of Pharm. Sciences vol. 86, No. 12, pp. 1458-1463 (1997).
Carbon Dioxide: Temperature—Pressure Diagram, 1999, ChemicalLogic Corporation.
DuPont, Freon 11, http://www.dupont.com/msds/40__37__2090fr.html, printed Feb. 21, 2002, 8 pages.
DuPont, Freon 113 Refrigerant, Material Safety Data Sheet, revised Apr. 20, 2004, 8 pages.
DuPont, Freon 12, Material Safety Data Sheet, revised Apr. 19, 2004, 7 pages.
Han et al., Density, Viscosity, and Excess Properties for Aqueous Poly(ethylene glycol) Solutions from (298.15 to 323.15) K, J. Chem. Eng. Data, 2008, 53, pp. 2598-2601.
Perry's Chemical Engineers' Handbook (2007) 7th Edition, 3 pages.
Salocks et al., Freon®, Technical Support Document: Toxicology Clandestine Drug Labs/Methamphetamine, vol. 1, No. 11, revised Sep. 24, 2003, 14 pages.

* cited by examiner

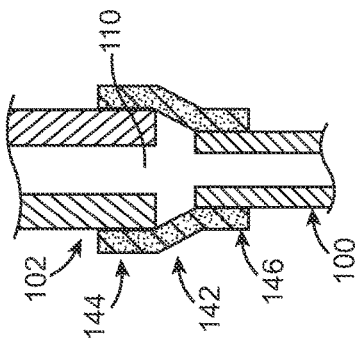
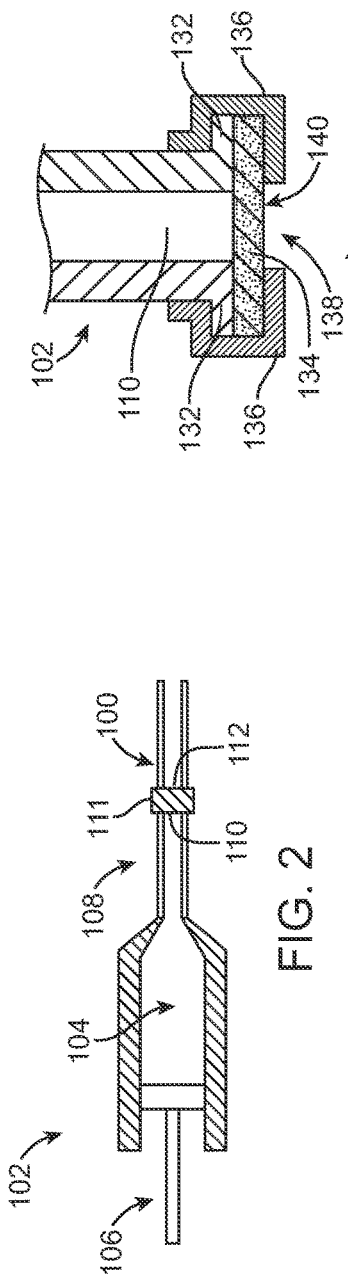
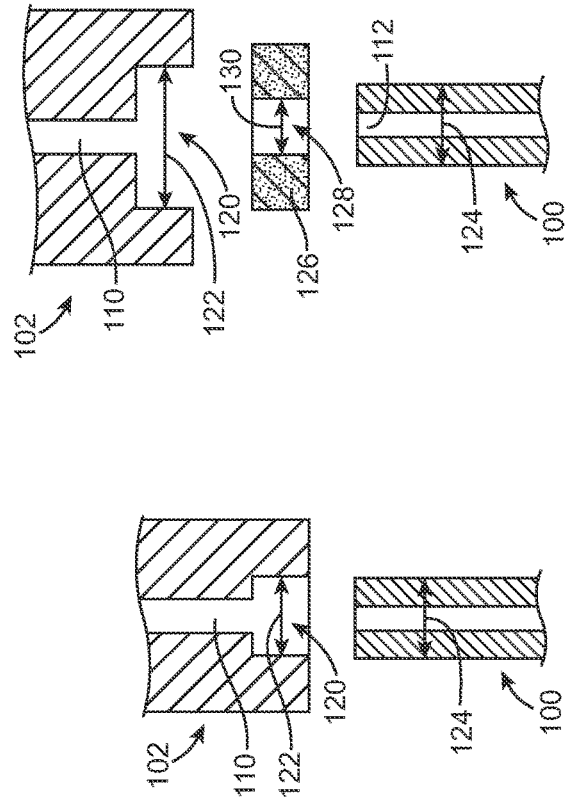

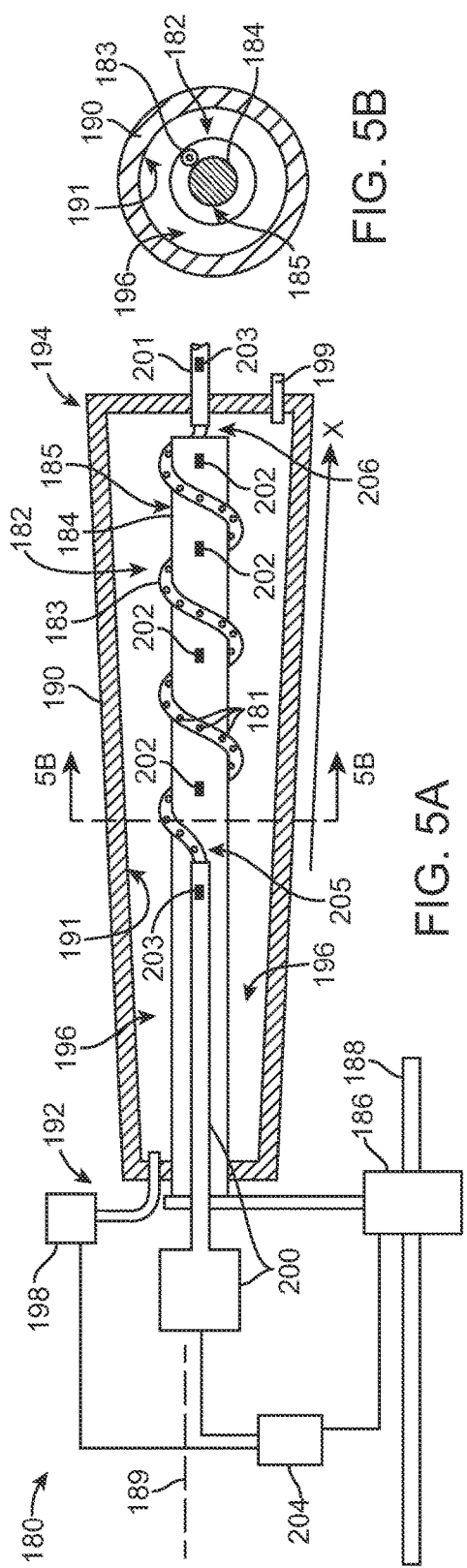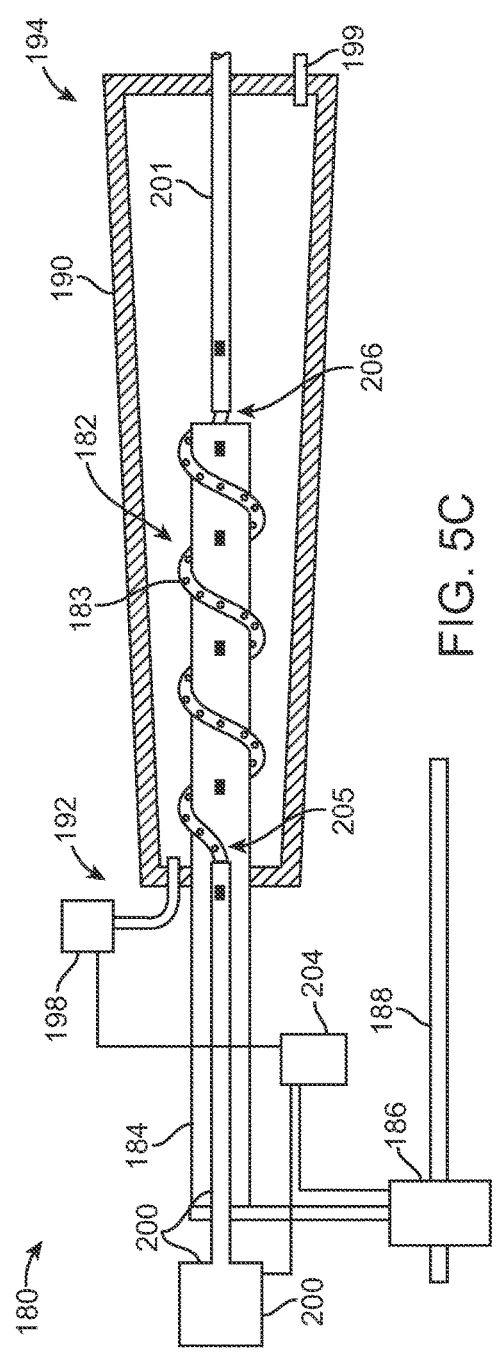

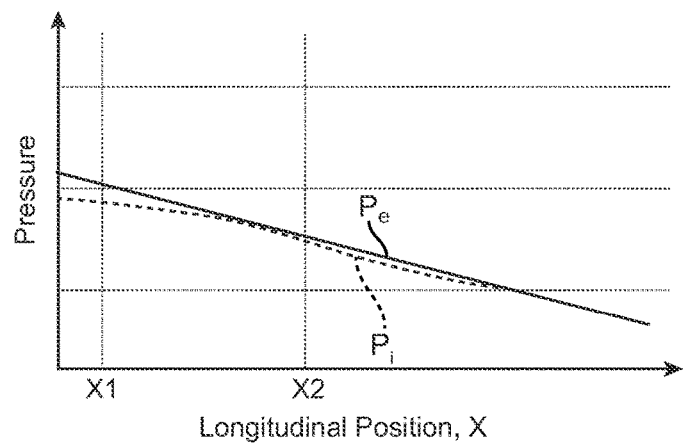
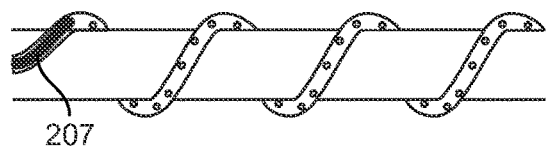
FIG. 5D
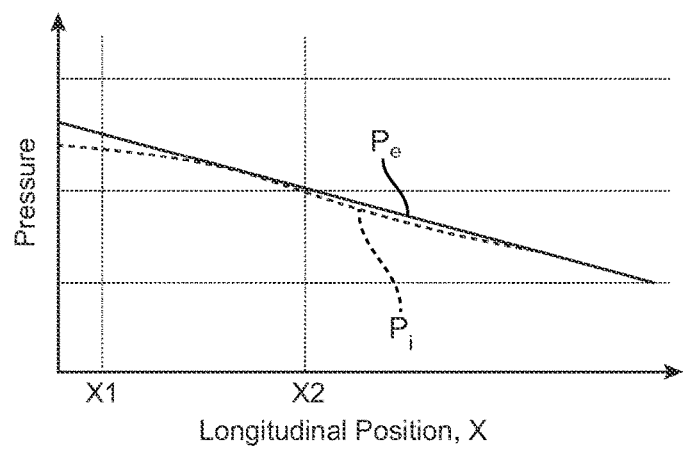
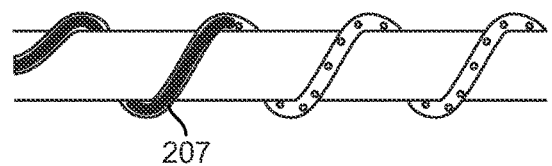
FIG. 5E

PRESSURE CHAMBER AND APPARATUS FOR LOADING MATERIAL INTO A STENT STRUT

FIELD OF THE INVENTION

This invention relates to an apparatus for depositing a composition within a structural element of a stent.

BACKGROUND OF THE INVENTION

The discussion that follows is intended solely as background information to assist in the understanding of the invention herein; nothing in this section is intended to be, nor is it to be construed as, prior art to this invention.

Until the mid-1980s, the accepted treatment for atherosclerosis, i.e., narrowing of the coronary artery(ies), was coronary by-pass surgery. While effective and evolved to a relatively high degree of safety for such an invasive procedure, by-pass surgery still involves serious potential complications, and in the best of cases, an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it another problem, elastic recoil of the stretched arterial wall which could undo much of what was accomplished and, in addition, PTCA failed to satisfactorily ameliorate another problem, restenosis, the re-clogging of the treated artery.

The next improvement, advanced in the mid-1980s, was use of a stent to hold the vessel walls open after PTCA. This for all intents and purposes put an end to elastic recoil but did not entirely resolve the issue of restenosis. That is, prior to the introduction of stents, restenosis occurred in 30-50% of patients undergoing PTCA. Stenting reduced this to about 15-30%, much improved but still more than desirable.

In 2003, the drug-eluting stent (DES) was introduced. The drugs initially employed with the DES were cytostatic compounds, compounds that curtailed the proliferation of cells that contributed to restenosis. As a result, restenosis was reduced to about 5-7%, a relatively acceptable figure. Today, the DES is the default industry standard for the treatment of atherosclerosis and is rapidly gaining favor for treatment of stenoses of blood vessels other than coronary arteries such as peripheral angioplasty of the popliteal artery.

The DES used today have a drug-polymer coating on the exterior surface of the stent. The inclusion of the drug in a polymer matrix allows for sustained delivery over time. One of the limitations of DES is the amount of drug that may be contained in a coating on a device. Another potential drawback is that the polymers used in the coating may contribute to an inflammatory response when the stent is implanted. Depending on the mechanical properties of the coating, it may become damaged during aggressive delivery procedures such as treating calcified lesions, or delivering the DES through a previously deployed stent. Also, the crimping of a DES onto a delivery device, such as the balloon of a catheter, must be done carefully to avoid damaging the coating.

Some alternatives to DES are stents with depots or channels in the structural elements, or struts, of the stent, or stents with some structural elements that are hollow tubes. Therapeutic agents or a composition including therapeutic agents may fill the interior of the hollow tube or a channel or depots. However, there are a number of challenges involved with filling such a hollow stent or depots with a composition including a therapeutic agent.

There is a continuing need for methods of filling the interior of a hollow structural element of a stent and one or more types of apparatus that may be used in such methods.

SUMMARY OF THE INVENTION

Briefly and in general terms, the present invention is directed to an apparatus for loading material into a stent strut.

In aspects of the invention, an apparatus comprises a pressure chamber, a stent support, wherein either one or both of the pressure chamber and the stent support are configured to translate relative to the other, a gas supply configured to move gas through the pressure chamber, and an injector configured to deliver material to be loaded into a stent.

In aspects of the present invention, an apparatus comprises a pressure chamber, a stent support within the pressure chamber, a stent comprising stent struts formed from a tube, the tube having a lumen, an opening to the lumen, and a plurality of side openings to the lumen, wherein the injector is configured to deliver material through the opening and into the lumen, an injector configured to deliver material to be loaded into the lumen, and a controller configured translate either one or both of the pressure chamber and the stent such that the stent moves through a pressure gradient when gas is moved through the pressure chamber.

The features and advantages of the invention will be more readily understood from the following detailed description which should be read in conjunction with the accompanying drawings.

DESCRIPTION OF THE DRAWINGS

FIG. 2 depicts an exemplary injector.

FIGS. 3A-3D depict several methods of coupling an injector to a tube.

FIGS. 5A-5C depict a device for use when injecting a composition into the lumen of a stent with hollow struts.

FIGS. 5D and 5E depict internal and external pressure gradients as a fucntion of longitudinal position within a coiled tube.

DETAILED DESCRIPTION

Figure 1A:
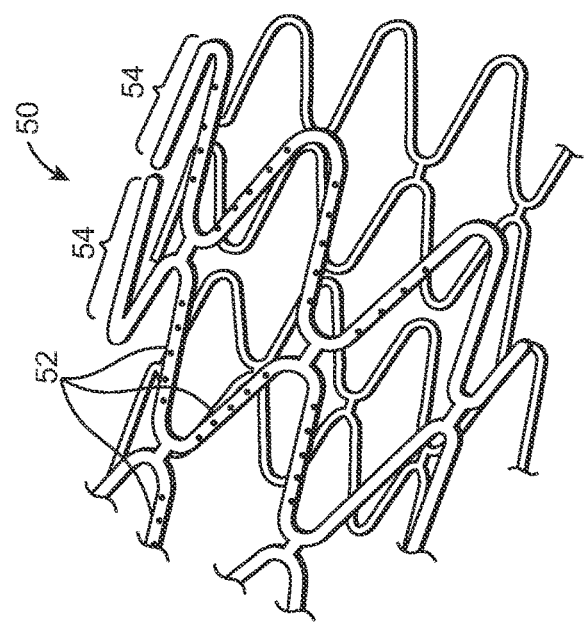
FIG. 1A depicts an exemplary and non-limiting embodiment of a stent with hollow struts.

Use of the singular herein includes the plural and vice versa unless expressly stated to be otherwise. That is, "a" and "the" refer to one or more of whatever the word modifies. For example, "a stent" may refer to one stent, two stents, etc. Likewise, "the polymer" may mean one polymer or a plurality of polymers. By the same token, words such as, without limitation, "stents" and "polymers" would refer to one stent or polymer as well as to a plurality of stents or polymers unless it is expressly stated or obvious from the context that such is not intended.

As used herein, words of approximation such as, without limitation, "about," "substantially," "essentially," and "approximately" mean that the word or phrase modified by the term need not be exactly that which is written but may vary from that written description to some extent. The extent to which the description may vary from the literal meaning of what is written, that is the absolute or perfect form, will depend on how great a change can be instituted and have one of ordinary skill in the art recognize the modified version as still having the properties, characteristics and capabilities of the modified word or phrase. In general, but with the preceding discussion in mind, a numerical value herein that is modified by a word of approximation may vary from the stated value by ±15%, unless expressly stated otherwise.

As used herein, any ranges presented are inclusive of the end-points. For example, "a temperature between 10° C. and 30° C." or "a temperature from 10° C. to 30° C." includes 10° C. and 30° C., as well as any temperature in between.

As used herein, a "polymer" refers to a molecule comprised of, either actually or conceptually, repeating "constitutional units." The constitutional units may derive from the reaction of monomers. As a non-limiting example, ethylene ($CH_2=CH_2$) is a monomer that can be polymerized to form polyethylene, $CH_3CH_2(CH_2CH_2)$—$CH_2CH_3$, wherein n represents an integer, and the constitutional unit is —$CH_2CH_2$—, ethylene having lost the double bond as the result of the polymerization reaction. A polymer may be derived from the polymerization of several different monomers and therefore may comprise several different constitutional units. Such polymers are referred to as "copolymers." The constitutional units themselves can be the product of the reactions of other compounds. As used herein, a molecule of more than 20 constitutional units is a polymer. Those skilled in the art, given a particular polymer, will readily recognize the constitutional units of that polymer and will equally readily recognize the structure of the monomer from which the constitutional units derive. A polymer may be a linear chain, a branched chain, star-like or dendritic, or one polymer may be attached (grafted) onto another. Polymers may have a random disposition of constitutional units along the chain, the constitutional units may be present as discrete blocks, or constitutional units may be so disposed as to form gradients of concentration along the polymer chain. Polymers may be cross-linked to form a network.

An "oligomer" is a molecule comprised of, either actually, or conceptually, repeating constitutional units, but where the number of constitutional units is too small to be considered to be a polymer. As used herein, an oligomer is a molecule of 20 or fewer constitutional units.

As used herein, "biocompatible" refers to a material that both in its intact, that is, as synthesized, state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

As used herein, the terms bioresorbable, biodegradable, bioabsorbable, bioerodable, biosoluble, absorbable, and resorbable, as well as degradable, erodable, and dissolvable, are used interchangeably, and refer to materials that are capable of being completely eroded, degraded, either biodegraded and/or chemically degraded, and/or absorbed when exposed to bodily fluids, such as blood, and can be gradually resorbed, absorbed and/or eliminated by the body.

Conversely, a "biostable" material refers to a material that is not biodegradable.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed.

One form of implantable medical device is a "stent." A stent refers generally to any device used to hold tissue in place in a patient's body. Stents may be typically tubular shaped devices. Particularly useful stents, however, are those used for the maintenance of the patency of a vessel in a patient's body when the vessel is narrowed or closed due to diseases or disorders including, without limitation, tumors (m, for example, bile ducts, the esophagus, the trachea/bronchi, etc.), benign pancreatic disease, coronary artery disease such as, without limitation, atherosclerosis, carotid artery disease, peripheral arterial disease, restenosis and vulnerable plaque.

A "lumen" as defined by Webster's Medical Dictionary is the channel within a tube such as a blood vessel, or the interior of a hollow organ such as the intestine. The term lumen is usually an anatomical term. As used herein, the term "lumen" may be broader, and may not only refer to the anatomy of an animal, but may also refer to the channel inside a tube or a tubular shaped object.

As used herein, a "hole" is an opening or a channel in a material created by any one or more of a combination of etching, laser machining, mechanical machining, drilling, and conventional processes known by persons of ordinary skill in the art. The location of holes may be predetermined.

As used herein, a "pore" is an opening or channel in a material that naturally results from the properties of the material. The location of pores may not be pre-determined.

As used herein, the terms "pores" and "holes" will be used interchangeably unless expressly stated otherwise.

As used herein, a material that is described as a layer or a film (e.g., a coating) "disposed over" an indicated substrate refers to a coating of the material deposited directly or indirectly over at least a portion of the surface of the substrate. "Directly deposited" means that the coating is applied directly to the surface of the substrate. "Indirectly deposited" means that the coating is applied to an intervening layer that has been deposited directly or indirectly over the substrate. The terms "layer", and "coating layer" will be used interchangeably and refer to a layer or film as described in this paragraph. A coating may be one layer or more than one layer. Each layer may be formed by one or multiple applications of coating material. A coating and a coating layer are supported by the substrate. Unless the context clearly indicates otherwise, a reference to a coating, layer, or coating layer refers to a layer of material that covers all, or substantially all, of the surface, whether deposited directly or indirectly.

As used herein, a "therapeutic agent" refers to any substance that, when administered in a therapeutically effective amount to a patient suffering from a disease or condition, has a therapeutic beneficial effect on the health and well-being of the patient (an animal, including a human). A therapeutic beneficial effect on the health and well-being of a patient includes, but it not limited to: (1) curing the disease or condition; (2) slowing the progress of the disease or condition; (3) causing the disease or condition to retrogress; or, (4) alleviating one or more symptoms of the disease or condition.

As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "therapeutic agent" also refers to pharmaceutically acceptable, pharmacologically active derivatives of those agents specifically mentioned herein, including, but not limited to, salts, esters, amides, and the like. Substances useful for diagnostics are also encompassed by the term "therapeutic agent" as used herein.

As used herein, the terms "therapeutic agent," "drug," "bioactive agent", "biologically active agent," "biological agent," and "active ingredient," will be used interchangeably.

A "pharmaceutical formulation" may be a therapeutic agent in combination with a pharmaceutical excipient. A pharmaceutical formulation may be a solid, semi-solid, a gel, a liquid, a suspension, a powder, or another physical form. As used herein, a "pharmaceutical formulation" encompasses a therapeutic agent in combination with an excipient that is loaded into the lumen of a structural element of a stent, and which is intended to remain within the lumen of the structural element of the stent until implanted into a patient.

As used herein, an "excipient" may be a substance that is combined with a therapeutic agent to form a final dosage form. Excipients are non-toxic, and are typically inert, that is the excipient itself is not a therapeutic agent. Excipients typically perform a function such as acting as a binder for the therapeutic agent, a carrier or a diluent for the therapeutic agent, a permeation enhancer, or an antioxidant or stabilizer for the therapeutic agent. In some cases vitamins and/or minerals, which may have therapeutic uses themselves, may also be an excipient. One of skill in the art can readily determine if a vitamin or mineral is being used as an excipient in a pharmaceutical formulation, and/or if the vitamin or mineral is a therapeutic agent in the pharmaceutical formulation. Unlike a solvent which is removed from the final dosage form, an excipient is not removed, but remains part of the final dosage form.

As used herein, a "solvent" can be as a substance capable of dissolving, partially dissolving, dispersing, or suspending one or more substances to form a uniform dispersion and/or solution, with or without agitation, at a selected temperature and pressure, and which is not an excipient. The substance may be a liquid, a gas, or a supercritical fluid. A solvent herein may be a blend of two or more such substances. As used herein, a substance used as an excipient in a pharmaceutical formulation is not a solvent even if it is capable of dissolving, partially dissolving, dispersing, or suspending one or more substances to form a uniform dispersion and/or solution. As used herein, a solvent may be used as a processing aid in forming a pharmaceutical formulation, but is removed, or substantially removed, during processing and does not form part of the final pharmaceutical formulation (except for incidental residual solvent).

A "fluid," as defined by Merriam Webster dictionary, is a substance that tends to flow or conform to the outline of it's container. A fluid is a state of matter that includes gases, liquids, supercritical fluids, and plasma. As used herein, a fluid can be a substance having a viscosity as measured under the temperature and pressure of interest of 10,000 cP or lower. As used herein, a fluid can be a substance that would conform to the shape of its container within a time frame of minutes (up to an hour) under the force of gravity.

A solid is one of the three states of matter—gas, liquid, and solid. A "solid" as defined by the Merriam Webster dictionary, is a substance that does not flow perceptibly under moderate stress, has "a definite capacity for resisting forces" such as compression or tension "which tend to deform it," and "under ordinary conditions retains a definite shape and size." As used herein, a "solid" can be a substance of definite shape and size and that does not conform to the outline of it's container under the force of gravity. As used herein, a solid may be a substance that conforms to the outline of its container by breaking chemical bonds, requires extensive deformation as with a metal, or, if an elastic solid, a substance that conforms with the application of stress, but returns to its prior shape, or substantially its prior shape, when the stress is removed. A substance may be defined to be a solid at a specified temperature and pressure if it has a "viscosity" of greater than $10^{12}$ cP at that specified temperature and pressure.

A "semi-solid" as defined by Merriam Webster dictionary is "a substance having qualities of both a solid and a liquid; highly viscous." As used herein, a substance can be a "semi-solid" at a specific temperature and pressure if it is a fluid having a viscosity greater than 10,000 cP. As used herein, a semi-solid can be a substance that would conform to the shape of its container under high stress and/or over a long period of time (months or years).

As used herein, a "particle" may be a piece of matter of any shape held together by physical bonding of molecules, held together by chemical bonds, such as a cross-linked polymer network, held together by ionic interactions, an agglomeration of particles held together by colloidal forces and/or surface forces, or a piece of matter held together by any combination of agglomeration, surface forces, colloidal forces, ionic interactions, and chemical bonds. For the purposes of this disclosure, a particle may be defined as ranging in size from less than one tenth of a nanometer up to several centimeters in size. In addition, a particle may include one or more types of constituent molecules.

For a plurality of particles, the "average" diameter may be a number-average diameter, a surface area diameter, or a volume average diameter as the particles are typically not all the same size and shape. The determination of any of these diameters typically involves approximating the diameter of an individual particle as a sphere of the same surface area, same volume, etc. Dynamic light scattering or Photo Correlation Spectroscopy is often used to determine particle size distributions, and it determines a "Z average" diameter which is close to the volume average diameter. The methods of determining the size distribution of a plurality of particles and the average diameter thereof are known in the art.

The polydispersity of a plurality of particles is a measure of the narrowness or broadness of the distribution of the particle sizes around the average. The standard deviation, which is a well-known statistical measurement, may be suitable for a narrow particle size distribution. The average may be referred to as a d50. Other measures of polydispersity include the d10, and d90 which refer to the diameters representing the threshold where 10% of the distribution falls below the d10, and 90% of the distribution falls below the d90, respectively. As an example, if the distribution is a distribution by number, at the d50, half or 50% of the number of particles have a diameter less than the d50. For an area average diameter, the d50 represents the diameter where half the surface area represented by the plurality of particles is below the d50, and half the surface area represented by the plurality is above the d50. Likewise, for a mass or volume distribution, 50% of the mass or volume is below the d50, and 50% of the mass or volume represented by the plurality of particles is above the d50.

Aspects of the present invention are directed to methods of loading or filling the lumen of a structural element of a stent. These are not methods for filling a lumen of a structural element of a stent once the stent is implanted, that is the in vivo filling of the lumen of a structural element, but are methods used prior to packaging the stent, and prior to implantation of the stent. These methods could be used before, or after, the stent is crimped onto the delivery catheter. As noted previously, a stent can be any device used to hold tissue in place in a patient's body. A stent can be a tubular shaped device formed of a scaffolding of a plurality of interconnecting structural elements, or struts. Other variations of stents include coiled or helical stents, and fibers or filaments forming the structural elements of the stent. It is the scaffolding that provides support or outward radial force to support tissue, such as a vessel wall, when implanted. The pattern of the scaffolding, or stent pattern, can be designed so that the stent can be radially compressed (crimped) and radially expanded (to allow deployment). The cross-section of the stent and/or the structural elements forming the stent is not limited to a circle, but may be elliptical or some other cross-section. Typical stent dimensions for an expanded coronary stent can be 2 to 5 mm in diameter, and 6 to 50 mm in length. Typical dimensions for an expanded peripheral stent are 3 to 8 mm in diameter, 8 mm to 20 mm in length, and about 80 microns to 250 microns in thickness. Aspects of the present invention are directed to stents in which at least some of the structural elements, which may be struts, have a lumen, or in other words, the struts can be, for example, essentially hollow cylinders.

Referring now in more detail to the exemplary drawings for purposes of illustrating embodiments of the invention, wherein like reference numerals designate corresponding or like elements among the several views, there is shown in FIG. 1A an exemplary stent 50 comprising a plurality of interconnected stent struts 52 configured to move relative to each other. The stent struts 52 can be, for example, arranged in a sinusoidal or serpentine pattern. The stent struts 52 can form a plurality of circumferential rings 54 that may be arranged axially to form a tubular scaffold configured to support biological tissue after implantation of the stent. The rings may be connected by as few as one linking strut per ring, but two, three, or more be present, or many more as depicted in FIG. 1. Surfaces of the tubular scaffold that face radially inward are referred to collectively as the luminal surface of the stent. Surfaces of the tubular scaffold that face radially outward are referred to collectively as the abluminal surface of the stent. The abluminal surface is a tissue contacting surface for a stent used in a blood vessel. In some embodiments, the structural elements forming the scaffold have sidewall surfaces that connect the abluminal and luminal surfaces. The "outer surface" of a stent may be any surface that would be in contact with tissue or blood when implanted in a patient and therefore includes abluminal and luminal surfaces and if present, sidewall surfaces. The pattern shown in FIG. 1A is an exemplary embodiment, and the embodiments of the invention are not limited to what has been illustrated as other stent patterns are easily applicable. Specifically, a stent which is a helix and/or coil is an alternative configuration. The stent may be comprised of individual ring sections, or made of one length of wire.

The rings 54 can be configured to be collapsed to a smaller diameter, thereby allowing the stent to be crimped onto a balloon or other device for delivering the stent to the desired implantation site within a patent. The rings 54 can be also configured to expand when inside the patient. The rings 54 can be expanded by inflation of a balloon on which the stent has been crimped, or alternatively, the rings can self-expand like a spring upon removal of an outer sheath.

Figure 1B:
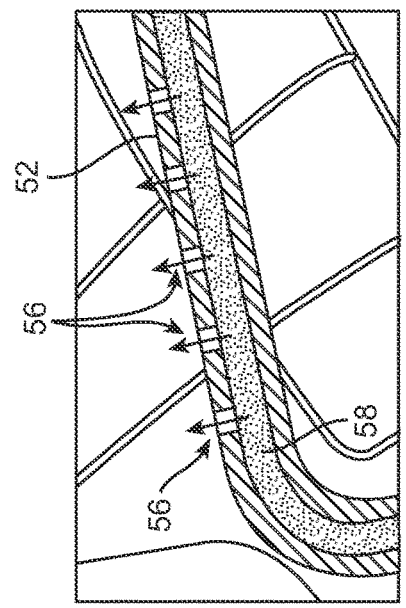
FIG. 1B depicts a close-up of a hollow strut of an exemplary embodiment of a stent.

Each strut 52 and ring 54 may be, for example, made of a continuous tube of material, a cross section of which is shown in FIG. 1B. The struts 52 formed from the continuous tube are referred to herein as "strut tubes." These strut tubes are exemplary, but not limiting, structural elements of a stent. Although the exemplary stent is shown with a struts have a circular or essentially circular cross-section, the cross-section of struts or structural elements is not limited to these, and may be elliptical, polygonal, rectangular, etc. The tube stock used to make the struts can be made from an extrusion process or other processes known in the art for making tube stock. Although the precise dimensions of the tube stock may vary depending upon the intended use of the stent, suitable tube stock diameters and wall thicknesses for coronary use may be between 40 and 200 microns and 10 to 80 microns, respectively. The tube stock is essentially uniform in diameter and cross-section over its length, but in some embodiments, the diameter and internal cross-section may vary or fluctuate over the length of the tube. To make the stent, the tube stock may be bent into the serpentine pattern, then wrapped around circumferentially to form the ring. Thus, bending may result in a change both the shape of the cross section as well as the internal cross-sectional area. A plurality of the rings can be made from a single, continuous tube. Alternatively, each ring can be made from its tube, and the rings can be connected by welding or bonding the tubes together or by attaching links to adjacent rings. In either case, there can be openings at one or both ends of the tube providing access to the lumen. In some embodiments, one opening at the end of the tube may be sealed, or plugged.

In the discussion that follows a reference to a strut tube or a structural element for use in a method or use with an apparatus or the like is not so limited and embodiments of the invention also encompass the use of a stent instead. Likewise, methods and apparatus that refer to a stent in the description are not so limited and embodiments of the invention also encompass the use of the strut tubes or structural elements instead of the stent. As an example, and without limitation, the disclosure of immersing a structural element having a lumen into a material encompasses both immersion of an individual ring or strut tube into the material as well as the immersion of an entire stent having a strut tube.

A plurality of holes and/or pores, referred to hereinafter as side openings 56, exist in the strut tubes. In one aspect of the invention, the side openings may be pores and may not include holes formed at predetermined locations. In another aspect of the invention, the side openings may be holes formed at pre-determined locations and not include any pores. In still another aspect, the side openings may be a combination of pores and holes formed at pre-determined locations. Each side opening 56 accesses the lumen of the strut tube 52 so that any composition 58 carried inside the lumen can escape out of the openings after the stent is implanted (as depicted by arrows in FIG. 1B). The composition may include a therapeutic agent. One or more of the side openings are in fluid communication with each other through the internal lumen. Although the side openings are illustrated as essentially circular in cross-section, the cross-section is not so limited and the openings may be of any shape or any combination of shapes, such as, without limitation, elliptical, rectangular, circular, or polygonal. The side openings extend from the internal surface or luminal surface of the strut tube to the exterior surface of the strut tube. The side openings may be in the abluminal, luminal, and/or sidewall surfaces of the strut. The side opening may be in the form of a channel with a uniform or substantially uniform cross-section, or the cross-section may vary. The aspect ratio of the opening may be 1, from 1 to 10, or in some cases greater than 10. The aspect ratio is the width to height of an object, or more generally, the ratio of longest dimension and the shortest dimension of an object.

The side openings may be of a diameter that is significantly smaller than that of the openings at the ends of the tube if end openings are present. In some embodiments, the size of an individual side opening, as determined by the area of the side opening on the internal surface of the tube is not more than 50% of the cross-sectional area of the opening at the end of the tube. As used herein "not more than 50% of the cross-sectional area of the opening at the end of the tube" means the smaller of the areas if the two end openings are present and do not have the same cross-sectional opening area. In an aspect of the present invention, this ratio is not more than 25%, and in still another aspect of the invention, not more than 10%. In another aspect of the invention, this ratio is not more than 5%. The side openings may be distributed along the length of each structural element. There may be about 4 to 144 side openings per ring. The distance between the side openings may be uniform or non-uniform.

Polishing and cleaning can be performed after the side openings 56 are formed in order to remove debris, burs and/or sharp edges. The side openings 56 can be made before or after the stock tube is formed into the struts and rings of the stent. Initially, the stock tubes are hollow and contain no material. After completion of the manufacturing process, the strut tubes 52 contain a composition 58 which may include therapeutic agent and/or other substances, some of which it may be desired to be released out from the stent after implantation. The composition can be filled in before or after the stock tube is formed into the struts and rings of the stent. The composition can be filled in before or after the side openings 56 are formed. Processes for tube bending, creating the side openings, polishing and cleaning may generate heat, involve the application of heat to the tube, or use corrosive chemicals. Therefore, when the composition to be filled into the tube is heat sensitive, prone to degradation when exposed to heat, or susceptible to the chemicals used, it is preferred to load the tube with the composition after the tube has been formed into the struts and rings of the stent, after the side openings are formed, and after any polishing.

The tubes, or the structural elements, used to form a stent are generally made from a biocompatible metal or metal alloy. Exemplary metals and metal alloys include, without limitation, cobalt-chromium alloys (e.g., ELGILOY™, Haynes alloy 25™, L605) stainless steel (316L), "MP35N," "MP20N," ELASTINITE™ (nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. The tube or structural elements may be made from a biostable polymer, a bioabsorable polymer, or a combination of a biostable polymer and a bioabsorbable polymer. The tubes may be made from other materials such as ceramics, and/or glass. Any of the above materials may be used in combination.

As noted above, the lumen of the strut tube is intended to be filled, or loaded, with one or more substances, hereinafter a "composition." Thus the substance filling or loaded into the strut tube lumen and which are intended to remain there until the stent is implanted may be referred to as a composition, and may include a therapeutic agent, and/or other substances. There are a number of challenges in filling such a lumen of a strut tube with a therapeutic agent. First, a reproducible quantity of the therapeutic agent must be placed within the lumen of the stent or a strut tube used in forming the scaffolding of the stent because the stent as a whole must contain a reproducible amount or dosage of a therapeutic agent. Second, uniform loading of the therapeutic agents along the length of the stent is preferred. Third, the process used to load or fill the lumen must be accomplished with no or minimal (not more than 10%, preferably not more than 5%) degradation of the therapeutic agent. Fourth, the process must result in no or a reproducible quantity of therapeutic agent outside the stent, that is on the outer surface, that is luminal, abluminal, and/or sidewall surfaces of the stent. Finally, the pharmaceutical formulation of the therapeutic agent must be shelf-life stable. The pharmaceutical formulation must also be released in vivo in a reproducible manner.

One manner of loading the composition into the lumen of the strut tube may be to inject the composition into the openings at the end of the strut tube, whether the strut tube forms one or multiple rings. Alternatively, the composition may be injected into the plurality of side openings instead of or in addition to injection into the one or both openings at the ends of the tube. In one embodiment, the composition is only introduced through the side openings as there are no openings at the ends of the tube. In a preferred embodiment, if injection is used, the composition may be injected into one or both openings at the end of the tube.

FIG. 2 shows an injector for injecting a material into a tube 100 either before or after the tube has been formed into struts and rings of the stent, before or after openings are formed into the tube, and before or after cleaning and polishing of the tube. The material injected may be a composition that is to be loaded into the lumen. Alternatively, the material injected may be a composition that has been dispersed in and/or dissolved in a solvent to form a solution that is injected leaving the composition in the lumen of the strut tube after removal of the solvent. The injector is a syringe 102 with a reservoir 104 containing the material. There is a piston or plunger 106 and a hypotube 108 at opposite ends of the reservoir. A discharge opening 110 of the hypotube is coupled to an inlet opening 112 at an end of the tube 100. A coupling 111 connects the discharge opening 110 and the inlet opening 112 together. Inward, axial movement of the plunger 106 causes the material in the reservoir 104 to be pushed out of the hypotube 108 and into the tube 100. The plunger 106 can be manually operated by a person or can be attached to a motor or other device to allow for precise control of movement and pressure. It will be appreciated that a variety of other types of injectors may be used to fill the tube instead of the syringe 102, including without limitation, a circumferential-piston pump, a diaphragm pump, a centrifugal pump, and a peristaltic pump.

An injector can be coupled to a tube in a number of ways, as shown in FIGS. 3A-3D. In FIG. 3A, a discharge opening 110 of an injector 102 is disposed at the bottom of a counterbore 120 formed into the tip of the injector. In this embodiment, the counterbore 120 functions as a coupling between the discharge opening 110 and the tube 100. The counterbore 120 is a cylindrical, flat-bottomed hole which enlarges the discharge opening 110. The cylindrical walls of the counterbore 120 are sized to have an inner diameter 122 that is substantially the same as or slightly smaller than an outer diameter 124 of the tube 100. When the tube 100 is inserted into the counterbore 120, the cylindrical walls provide a tight, friction fit or compress the tube 100 to prevent leakage of the material being injected into the tube.

In FIG. 3B, an inner diameter 122 of cylindrical walls of a counterbore 120 are much greater than an outer diameter 124 of a tube 100. An annular gasket 126 made of elastic material is inserted into the counterbore 120. In this embodiment, the gasket 126 functions as a coupling between the discharge opening 110 and the tube 100. A through-hole 128 at the center of the gasket 126 is sized to have an inner diameter 130 that is slightly smaller than the outer diameter 124 of the tube 100. When the tube 110 is inserted into the through-hole 128, the gasket 126 deforms and forms a fluid-tight seal around the tube 110. Various gaskets having different sized through-holes can be used to allow the injector 102 to be used to fill tubes of varying diameters.

In FIG. 3C, an injector 102 has a discharge opening 110 surrounded by an annular flange 132 on which a flat, circular membrane or gasket 134 is attached by a round cap 136. In this embodiment, the gasket 134 functions as a coupling between the discharge opening 110 and the tube 100. The cap 136 has a central hole 138 that exposes a surface 140 of the gasket 134. The central hole 138 is sized larger in diameter than the tube 100 to allow the injector to be used to fill other tubes with different diameters. The exposed surface 140 of the gasket 134 initially has no hole. The gasket 134 is made of an elastic material that can be punctured by a tube 100. When the tube 100 is pushed through the gasket 134, the opening 112 of the tube is disposed inside the discharge opening 110 of the injector 102, and the gasket 134 forms a fluid-tight seal around the tube 110. The end of the tube can be cut at a bias or angle so as to produce a sharp point for piercing into the gasket 134. When the tube 100 is pulled out of the gasket 134, the gasket 134 self-seals the hole left behind by the tube 100, thereby preventing spillage of the material inside the discharge opening 110.

In FIG. 3D, an elastic coupling sleeve 142 connects an ejector 102 to a tube 100. The elastic coupling sleeve 142 has a first opening at a first end 144 of the sleeve and a second opening at a second end 146 of the sleeve. The first opening at the first end 144 has an inner diameter that is smaller than the outer diameter of the injector tip so that when the injector tip is inserted into the first opening, as shown in FIG. 3D, the first end 144 is sealed tightly around the discharge opening 110 of the injector 102. The second opening at the second end 146 has an inner diameter that is smaller than the outer diameter of the tube tip so that when the tube tip is inserted into the second opening, as shown in FIG. 3D, the second end 146 is sealed tightly around the inlet opening 112 of the tube 110.

The material that is injected may be in the form of a solid powder. Preferably, the material is a composition that is a fluid. In one embodiment, the composition may be a therapeutic agent that has been melted, and is then injected into the strut tube while molten, and subsequently solidifies within the tube. The therapeutic agent may be heated until it melts, and then injected into the inlet opening and/or another opening to fill the lumen of the strut tube. As used herein, the phrases, "load the strut tube," "load the lumen of the strut tube," "fill the strut tube" and "fill the lumen of the strut tube," encompass both partially and completely filling the lumen of the strut tube.

Therapeutic agents that are stable, or reasonably stable, in the melt, and which possess characteristics such that when at a temperature of about 30° C. and a pressure of about one atmosphere, the therapeutic agents are solids or semi-solids may be used. Therapeutic agents that are solid or semi-solid at a temperature of about 30° C. and a pressure of about one atmosphere may be solids or semi-solids at temperatures below about 30° C. and at pressures above about one atmosphere. As used herein, "reasonably stable," refers to a therapeutic agent that may be injected as a melt with not more than 5% degradation occurring during the process, preferably not more than 2%. Percent degradation refers to a decrease in the purity and/or content of the therapeutic agent. In some embodiments, the therapeutic agent may be a solid or a semi-solid at 25° C. and at one atmosphere, but may be a fluid above 25° C. at one atmosphere. In still other embodiments, the therapeutic agent is one which is a fluid with a viscosity of not less than 10 cP, preferably not less than 100 cP, more preferably not less than 1000 cP, and even more preferably not less than 5000 cP, at about 30° C. and a pressure of about one atmosphere. Such fluids will have a higher viscosity at temperatures less than about 30° C. at about one atmosphere. The viscosity of the composition that fills the lumen of the strut tubes that can be utilized may be a function of the size of the side openings with smaller side openings allowing for a lower viscosity fluid to be used as the composition. Examples of therapeutic agents which may be melted and injected include, without limitation, paclitaxel, protaxel, dexamethasone, momentasone, clobetasol, and dexamethasone acetate. A combination of therapeutic agents may be used in any of the embodiments of the present invention.

If the therapeutic agent to be used is not reasonably stable when melted, then the composition may be a pharmaceutical formulation incorporating the therapeutic agent and a low melting excipient such that the pharmaceutical formulation can be injected into the strut tubes. The low melting excipient may be melted and the therapeutic agent may be dissolved or dispersed in the excipient to form a pharmaceutical formulation. The pharmaceutical formulation may be then injected into the strut tube. The viscosity of the Examples of therapeutic agents that may be used in the low melting excipient pharmaceutical formulations include, without limitation, zotarolimus, everolimus, sirolimus, biolimus, deforolimus, novolimus, myolimus, temsirolimus, and any combination thereof.

In some embodiments, a low melting excipient may be an excipient which melts at not more than 60° C. when at one atmosphere pressure. In other embodiments, a low melting excipient may be one which melts at not more than 55° C. when at one atmosphere pressure. In still other embodiments, a low melting excipient may be one which melts a temperature of not more than 50° C., a temperature of not more than 45° C., or a temperature of not more than 40° C. when at one atmosphere pressure. The excipient may be chosen such that the when used in the appropriate amount in the final pharmaceutical formulation the result is a pharmaceutical formulation that is a solid or semi-solid when the pharmaceutical formulation is at about one atmosphere pressure and at 30° C., and the pharmaceutical formulation is also a solid or semi-solid at temperatures lower than 30° C. at a pressure of about one atmosphere. Therefore, the lower limit on the melting temperature may be about 30° C., and preferably about 35° C. In some embodiments, the low melting excipient has a melting temperature of above body temperature, about 37° C. for a human, and in some embodiments, the low melting excipient has a melting temperature of about body temperature.

Excipients chosen for use in a composition that to be loaded into the lumen of a strut tube and is a pharmaceutical formulation with a low melting excipient previously described as well as those pharmaceutical formulations to be described subsequently, may be biocompatible, compatible with the therapeutic agent, and shelf-life stable in combination with the therapeutic agent.

Examples of low melting excipients include, without limitation, solid poloxamers, TWEEN™ 60 (polysorbate 60), Vitamin E TGPS, PLURONIC® F68, PLURONIC® F127, Poloxamer 407, ascorbyl palmitate, lecithin, egg yolk phospholipid, phosphatidylcholine, polyethylene glycol-phosphatidyl ethanolamine conjugate (PEG-PE), polyethylene glycol, triglycerides, diglycerides, monoglycerides, fatty alcohols such as aliphatic alcohols having a chain of 8 to 22 carbon atoms, and any combination thereof. Vitamin E TPGS is also known as D-alpha tocopheryl polyethylene glycol 1000 succinate, and is a water soluble form of Vitamin E. A specification for Vitamin-E TPGS is listed in the United States National Formulary (NF). Polysorbates are a group of oleate esters of sorbitol and its' anhydrides condensed with polymers of ethylene oxide. Polysorbates are used as emulsifiers and surfactants in food, pharmaceuticals and cosmetics. Examples include polysorbate 20, polysorbate 60, and polysorbate 80, the specifications of which are all listed in the United States Pharmacopeia (USP). PLURONIC® is a trade name of BASF and encompasses a group of block copolymers formed from ethylene oxide and propylene oxide. Poloxamers are copolymers with a central block of polypropylene oxide) (PPO) and with a block of poly(ethylene oxide) (PEO) on each side where the PEO blocks are usually of the same length as determined by the number of constitutional units. Poloxamers of types 124, 188, 237, 338, and 407 are specified by a monograph in the National Formulary. Many of the PLURONIC® polymers are surfactants, and some of them also comply with one of the NF monographs for Poloxamers.

Excipients used in a composition to be loaded into the lumen of a strut tube including the composition which is a pharmaceutical formulation with a low melting excipient described above and all of the compositions to be described subsequently, may be chosen to facilitate release of the therapeutic agent from the strut tube after implantation in a patient. In some embodiments, an excipient may be chosen to increase the dissolution and/or release rate of a therapeutic agent, or to decrease the dissolution and/or release rate of a therapeutic agent. For example and without limitation, the excipient PFE-PE would be expected to increase the dissolution of a hydrophobic drug. As another example, without limitation, the triglyceride glycerol-tristearate would be expected to decrease the dissolution of hydrophilic drug.

A sustained release of a therapeutic agent over time may be when not more than 80% of the drug is released in the first 12 hours post implantation, 24 hours post implantation, 36 hours post implantation, or first week post implantation. In some embodiments, sustained release of a therapeutic agent over time may be 80% of the drug will have been released in a time frame ranging from 24 hours post implantation to 72 hours post implantation.

The pharmaceutical formulation with a low melting excipient may include between about 2 weight % (wt %) and about 90 wt %, preferably between about 5 wt % and about 50 wt %, and even more preferably 10 wt % and 35 wt % therapeutic agent. The pharmaceutical formulation may include other exicpients in addition to the low melting excipient such as, without limitation, stabilizers, anti-oxidants, lubricants, carriers, and/or diluents.

In some embodiments, even if the therapeutic agent is reasonably stable in the melt, the composition that is loaded into the lumen of a strut tube may be the therapeutic agent combined with an excipient to form a pharmaceutical formulation. If the therapeutic agent is one which is reasonably stable in the melt, the excipients added may function as a diluent to control the dose, facilitate dissolution, or retard dissolution. Other types of excipients that may be used include those types that are typically used in pharmaceutical formulations. Examples include, without limitation, stabilizers, anti-oxidants, lubricants, and/or carriers. Thus, in some embodiments including a reasonably stable therapeutic agent, the composition injected will be about 98 wt %, about 99 wt %, or about 100 wt % therapeutic agent, or will consist essentially of the therapeutic agent. In other embodiments, the composition may be a pharmaceutical formulation that is to be injected, the pharmaceutical formulation may include between about 50 wt % and 99 wt % therapeutic agent, preferably between 60 wt % and 98 wt % therapeutic agent, and more preferably between 65 wt % and 95 wt % therapeutic agent. It is understood that therapeutic agents "as received," or as used or as added to a pharmaceutical formulation, do not assay at 100% therapeutic agent, but may contain up to about 5% incidental impurities or other substances.

During the injection, and optionally for some time after the completion of the injection, the stent, or strut tube, and the composition within the lumen and/or within the injector may be maintained at a temperature, or within a temperature range, sufficient to maintain the composition in a fluid state. The temperature may fluctuate or change provided that the composition remains in a fluid state. In some embodiments, the stent or strut tube may be maintained at and/or above a specific temperature during the injection, and optionally for some period of time after the injection, where the specific temperature may be 30° C., 35° C., 40° C., or 45° C. In other embodiments, the specific temperature may be the melting temperature of the therapeutic agent, the melting temperature of the pharmaceutical formulation, or the melting temperature of the excipient, or higher, and in still other embodiments, the specific temperature may be 5° C., 10° C., or 15° C. higher than the melting temperature of the therapeutic agent, the pharmaceutical formulation, or the excipient. During the operation of melting the therapeutic agent or dissolving and/or dispersing the therapeutic agent in the molten excipient, as well as during the injection of the composition which may be a therapeutic agent or pharmaceutical formulation thereof, the temperature may not exceed a temperature, which may be referred to as a maximum temperature, at which significant degradation of the therapeutic agent may occur during the time period of the melting or dissolving/dispersing operation, and the injection operation. As used herein, "significant degradation" will be degradation of more than 5%. In some embodiments, a maximum temperature may be selected such that the degradation of the therapeutic agent is not more than 3%, and in still other embodiments, not more than 1%. Various embodiments of the invention encompass a maximum temperature of 60° C., 65° C., 70° C., and 80° C.

In some embodiments, the stent or strut tube and the composition within the lumen and/or injector may be maintained at a temperature, or within a temperature range, sufficient to maintain the composition in a fluid state with a viscosity of not more than 10,000 cP, preferably not more than 5000 cP, and even more preferably, not more than 100 cP during the injection. In still other embodiments, the, the stent or strut tube and the composition within the lumen and/or injector may be maintained at a temperature, or within a temperature range, sufficient to maintain the composition in a fluid state with a viscosity in the range of about 5 cP to about 10,000 cP, but preferably in the range of 5 cP to about 100 cP. The viscosity may be determined using a capillary rheometer, cone and plate viscometer, capillary viscometer, cuette viscometer, or falling ball viscometer. The fluid may be Newtonian or non-Newtonian. For excipients which are macromolecules, shear thinning behavior may be advantageous. In the case of non-Newtonian fluids, measuring the low or zero shear viscosity is the value most predictive of the fluid behavior during injection or loading as this will be a low flow rate process. Maintaining the strut tube and/or the injector containing the therapeutic agent or pharmaceutical formulation thereof at or within a specified temperature range may be accomplished by methods that are well-known in the art such as use of a heating jacket or coils, an infrared lamp, blow dryer, etc.

The injection of the composition, whether the composition is a molten therapeutic agent or the pharmaceutical formulation including a therapeutic agent in any of the embodiments described above, uses a pressure in the range of 10 to 15,000 $lb/in^2$. Other embodiments encompass a pressure in the range of 10 to 5,000 $lb/in^2$, 100 to 10,000 $lb/in^2$, 10,000 to 15,000 $lb/in^2$, or 12,000 to 15,000 $lb/in^2$.

In some embodiments, the injection may occur in an inert atmosphere, that is one free of oxygen or substantially free of oxygen (such as, for example and without limitation, <1000 ppm oxygen). In some embodiments, the injection occurs in an environment that is free of or substantially free of humidity (not more than 5% rh), or an environment of low humidity (between about 5% and not more than 20% rh).

In some embodiments, the injection may end when the composition is visible at the other inlet opening of the strut tube if present and if open. In some embodiments, the injection may end when a specified weight or volume of the composition has been added to the strut tube.

After the injection, the composition may be allowed to cool to room temperature, that is approximately 20° C. to 25° C. and one atmosphere. After cooling the composition, that is the therapeutic agent or pharmaceutical formulation thereof, is a solid or a semi-solid. In some embodiments, the semi-solid has a viscosity of not less than 15,000 cP, while in other embodiments, the viscosity may be not less than 10,000 cP. In still other embodiments, after cooling to room temperature, the composition is a fluid having a viscosity not less than 10 cp, preferably not less than 100 cP, more preferably not less than 500 cP, even more preferably not less than 1000 cP, and still even more preferably, not less than 5000 cP. The rate of decrease in the temperature of the stent or strut tube filled with the composition may be increased by the use of a fan, placement of the filled strut tube in an environment with an ambient temperature below 25° C., or use of a cooling coil which surrounds the strut tube and has a fluid flowing through the coil, the fluid being at a temperature below 25° C. Other methods of increasing the cooling rate include contact with an object of high thermal conductivity which is at a lower temperature, immersion of the filled stent in a fluid of a temperature lower than that of the stent, and immersion in an ice bath or other cooling bath. As used herein, the phrases, "cooling the strut tube" and "cooling the stent," will encompass both passive cooling, that is removing any source of heat, and allowing the stent to cool in the ambient surroundings without making any other changes to the surroundings, and active cooling, which includes, in addition to the removal of a heat source, taking one or more active measures to increase the rate of cooling, such as, for example and without limitation, using a fan, or another measure including, but not limited to, those described above.

The advantage of using a therapeutic agent in the melt, or a pharmaceutical formulation of a therapeutic agent in a molten or fluid state, is that the use of a solvent as a carrier is avoided. Thus, for the methods described above, the composition injected, whether a therapeutic agent alone or a pharmaceutical formulation thereof, is free of, or essentially free of, solvents. All of the composition that is injected remains, or essentially remains, inside the lumen of the strut tube. Residual solvent inside the strut tube may lead to stability issues for the therapeutic agent. The therapeutic agent may be degraded with time or the solvent content inside the strut tube may change with time which can lead to a change in the agent release rate. It is also undesirable to release solvents in vivo due to biocompatibility or toxicity issues.

In some embodiments, the internal lumen of the strut tube may be coated with or exposed to a lubricant prior to the injection. Examples of lubricants include, without limitation, silicone oil and various silicone fluids, liquid PEG, liquid mono-, di- and triglycerides, vegetable oils, glycerol propylene glycol, magnesium stearate, calcium stearate, zinc stearate, stearic acid, talc, and starch. The lubricant may be dissolved in a solvent or fluidized or atomized in air, another gas, or a fluid, which may be blown through the strut tube, or if present as liquid or fluid, may be injected into the strut tube, to deposit the lubricant onto the luminal surface of the strut tube. If a solvent is used, the solvent may be evaporated.

In another embodiment, the composition which may be a therapeutic agent or a pharmaceutical formulation thereof, may be dissolved or dispersed in, but preferably dissolved in, a solvent to form an injection solution. The injection solution may be injected into the lumen of the strut tube, and then the solvent may be removed leaving the composition in the lumen. Injection may be into one or both end openings, if present, and/or one or more side openings. Due to the small diameter of the lumen of the strut tube as well as the small size of the side openings about the surface thereof, the removal of the solvent may be difficult. Thus, the methods preferably use solvents that are in a gas phase at about 20° C. to 25° C. and one atmosphere, and therefore, readily evaporate.

The methods using an injection solution may involve changing the condition of temperature and/or pressure such that the injection solution is in a liquid or supercritical fluid state. The method may include a decrease in the temperature and/or an increase in the pressure such that the solvent and/or the injection solution is in a liquid or supercritical state. The injection solution may be then injected into the lumen of the strut tube under a condition of temperature and pressure that maintain the injection solution in a liquid or supercritical fluid state. Similar to the situation described previously, "maintain the temperature and pressure" allows for fluctuations in the temperature and pressure provided that the injection solution remains in a supercritical or liquid state. In some embodiments, the temperature and pressure may be maintained within a range such that density fluctuations of the injection solution are not more than 5%. Once the injection has been completed, the condition of temperature and pressure of the filled strut tube may be changed such that the strut tube and its contents are at about 20° C. to 25° C. and one atmosphere. At this temperature and pressure, the solvent is a gas, and the solvent will boil and dissipate through the side openings and/or the openings at the ends of the tube, leaving behind, or substantially leaving behind, in the lumen of the strut tube, the composition which is a therapeutic agent or a pharmaceutical formulation thereof. Because the solvent occupies some volume, more than one cycle of injecting an injection solution followed by a change in the condition of the strut tube and its contents may be required to fill the lumen with the desired quantity of the composition. Therefore, the cycle may be repeated one or more additional times. For example two cycles, three cycles, or more than three cycles may be performed.

One class of substances that may be used as solvents are those substances having a boiling point below room temperature, that is below about 20° C. to 25° C. at a pressure of one atmosphere. In some embodiments the solvent has a boiling point, measured at a pressure of one atmosphere, below 20° C., preferably below 10° C., more preferably below 0° C., and even more preferably below −10° C. Some examples of substances that may be used as solvents include, without limitation, propane, pentane, cyclopentane, butane, dimethylether, trifluoromethane, dichlorodifluoromethane, chlorodifluoromethane, 1,2-dichloro-1,1,2,2-tetrafluoroethane, 1-chloro-1,1-difluoroethane, FREON® solvents where FREON® is the trade name of DuPont for a number of chlorofluorocarbons, chlorofluorohydrocarbons, fluorohydrocarbons, and halons. Halons are hydrocarbons in which one or more hydrogen atoms are replaced with bromine, and other hydrogen atoms with other halogen atoms (fluorine, chlorine, and iodine). FREON® solvents include, HFC134a™, the trade name for 1,1,1,2-tetrafluoroethane ($CF_3CFH_2$), and HFC-227ea™, the trade name for 1,1,1,2,3,3,3-heptafluoropropane ($CF_3CHFCF_3$). HFC-134a has a boiling point of −26° C. HFC-227ea has a boiling point of −16° C. Both HFC-134a and HFC-227ea are used as propellants for medical aerosols. In some embodiments, supercritical carbon dioxide ($CO_2$) or another supercritical fluid may be used. In still other embodiments liquid $CO_2$ may be used.

The injection solution may be formed by either decreasing the temperature, and/or increasing the pressure of the solvent such that it is in either a liquid or supercritical state, and then dissolving or dispersing the therapeutic agent, and optionally an excipient into the solvent in this liquid or supercritical state to form the injection solution. In some embodiments, the solvent may be cooled to a temperature in the range of 20° C. to −60° C., for example and without limitation, to at least 5° C., at least 0° C., at least −10° C., at least −20° C., at least −30° C., at least −40° C., at least −50° C., or at least −60° C., while the pressure remains at about one atmosphere. In some embodiments, the solvent pressure may be increased to about 2 to about 32 atmospheres, for example and without limitation, at least 5 atmospheres, at least 10 atmospheres, at least 20 atmospheres, or at least 32.5 atmospheres. In still other embodiments, the addition of the therapeutic agent and the optional excipient result in boiling point elevation, or in other words, the injection solution thus formed has a boiling point that may be higher than that of the solvent alone.

The injection solution may include between 10 wt % and 99 wt % solvent, preferably between 20 wt % and 98 wt % solvent, and even more preferably between preferably 25 wt % and 95 wt % solvent. If the therapeutic agent is formulated with an excipient to form a pharmaceutical formulation, the therapeutic agent may be between 0.5 wt % and 99 wt % of the pharmaceutical formulation, preferably between 1 wt % and 98 wt %, and more preferably between 5 wt % and 95 wt %. The solvent is not intended to form part of the final pharmaceutical formulation even though some residual solvent may remain.

In some embodiments, the injection solution may include an additive or an excipient that causes the solution to have a contact angle of less than 90 degrees on the surface of the structural element to allow the solution to penetrate into the lumen with greater ease than if the additive were not present. In some embodiments, the injection solution may include a wetting enhancement fluid which allows the solution to have a contact angle of less than 90 degrees on the surface of the structural element to allow the solution to penetrate into the lumen with greater ease than if the wetting enhancement fluid was not present. An additive is another substance which may be added to the injection solution and/or to a composition which is not intended to remain in the lumen. In other words, it may be a solvent, or another substance, which is not incorporated, or not intended to be incorporated, into the composition that fills the lumen (except for residual incidental amounts). Similarly, a substance which causes the solution to have a contact angle of less than 90 degrees on the surface of a structural element to allow the solution to more easily penetrate the lumen that if the substance were not present but which substance is incorporated into the composition remaining in the lumen is an excipient. A wetting fluid may be a solvent, an additive, or an excipient. An additive may be a solvent. Examples of substances that may cause the solution to have a contact angle of less than 90 degrees include, but are not limited to, surfactants. Many surfactants are also excipients.

In some embodiments, the strut tube may be chilled to a temperature in the range of about 20° C. to −60° C. prior to injection of the injection solution, for example and without limitation, to at least 5° C., at least 0° C., at least −10° C., at least −20° C., at least −30° C., at least −40° C., at least −50° C., or at least −60° C., while the pressure remains at about one atmosphere. In some embodiments, the stent may be placed in an environment (e.g. pressure chamber) in which the pressure is increased to about 2 to about 100 atmospheres, for example and without limitation, at least 5 atmospheres, at least 10 atmospheres, at least 20 atmospheres, at least 32.5 atmospheres, or at least 73 atmospheres. In some embodiments, if there is more than one tube end opening, the other end opening may be plugged with a removable plug. Methods of plugging the end openings, and optionally side openings, are discussed below.

During the injection, the condition of temperature and pressure may be maintained such that the injection solution is in a liquid or a supercritical state. Thus, the temperature may be maintained to be not more than a specific temperature in the range of about 40° C. to about −60° C., such as, without limitation, not more than 10° C., not more 0° C., not more than −10° C., not more than −20° C., not more than −40° C., or not more than −60° C. The pressure may be at about 1 atmosphere or much higher than 1 atmosphere, such as between 72.9 and 100 atm. The lower limit on the temperature during the injection and optionally for some time subsequent thereto may depend upon the specific materials of construction of the strut tube, the injector and connectors, as well as the attributes of the composition, that is therapeutic agent and the optional excipient. In some embodiments, the lower limit on the temperature may be about −123° C. As an example and without limitation, the lower limit of the temperature may be one that would be below the glass transition temperature of material of a gasket, such as gasket 126 or gasket 134 discussed above, or of a sleeve, such as elastic coupling sleeve 142 discussed above as below the glass transition temperature these materials would become hard and brittle. In some embodiments the pressure may be maintained such that it does not fall below 100 atmospheres, below 73 atmospheres, below 32.5 atmospheres, below 20 atmospheres, below 10 atmospheres, or below 2 atmospheres. Also, the upper limit of pressure will depend upon the specific materials of construction of the stent and the dimensions of the strut tube, and the injector and any other apparatuses used in the injection, as well as the attributes of the composition to be loaded and the solvent. The upper limit on pressure may be about 50,000 lb/in$^2$.

The pressure required to effect the injection may be about 10 to about 10,000 lb/in$^2$ in excess of the pressure required to maintain the injection solution in a liquid or in a supercritical state. The injection solution may have a viscosity of not more than 10,000 cP but not less than 1 cP under the temperature and pressure conditions of the injection, but preferably the viscosity of the injection solution is not more than 100 cP.

The injection may be executed in an inert and/or low humidity environment in the same manner as described above for the other embodiments.

After the injection is complete, the condition of temperature and pressure may be changed such that the solvent boils and evaporates from the injection solution, leaving the therapeutic agent, or a pharmaceutical formulation comprising the therapeutic agent and the optional excipient, in the lumen of the strut tube. The evaporating solvent may incidentally carry with it some of the therapeutic agent and the optional excipient. In some embodiments, 90 wt % or more of the sum of the weights of the therapeutic agent and optional excipient that are injected into the strut tube lumen remain in the lumen after the solvent evaporates, while in other embodiments 95% wt % or more remains or 98 wt % or more remains. The change in the temperature may occur as a result of removing any coolant source, removing the strut tube and its contents from a bath or a cool environment and then allowing the strut tube and its contents to warm to about approximately 20° C. to 25° C., or the strut tube and its contents may be actively heated by known means until the temperature is approximately 20° C. to 25° C. In other embodiments, the strut tube and its contents are brought to a temperature of above 25° C., such as at least 30° C. or at least 35° C. Similarly, the pressure condition may be changed by moving the strut tube and its contents to a lower pressure environment or relieving a pressure valve, and then allowing the pressure to equilibrate to about one atmosphere. Alternatively, the pressure may be changed by pulling a vacuum. If the strut tube and its contents are in a closed chamber, both the temperature and pressure may be altered via a controller connected to the necessary valves and sensors that allow the condition of pressure and temperature to be changed.

The change in the temperature and pressure may occur gradually over a time period of 5 to 60 minutes, or may occur essentially instantaneously in less than one minute. The change in condition may occur by increasing the temperature followed by a decrease in pressure, or decreasing the pressure followed by an increase in temperature. In some embodiments, the temperature and pressure may change simultaneously, or may change such that there is some overlap in time between the time period over which the pressure change occurs and the time period over which the temperature change occurs.

As discussed above, when the composition is loaded by injecting an injection solution with subsequent evaporation of the solvent, more than one cycle may be required. Each cycle may use an injection solution of the same composition, that is the same wt % of the therapeutic agent and optional excipient. Alternatively, each cycle may use the same therapeutic agent and optional excipient, but the composition may differ in the wt % of the therapeutic agent and optional excipient. In yet another alternative, the injection solution may differ because the solvent is different, the therapeutic agent is different, and/or the optional excipient is different. As used herein, a "different therapeutic agent" covers the situation in which the two agents only differ because one is a salt, different salt, a hydrate, a different hydrate, or a polymorph of the other, as well as the situation in the pharmacological activity of the two agents is the result of a different chemical entity. With respect to the multiple injection cycles, the injection solution in a cycle after the initial cycle may be near or at saturation of the therapeutic agent and/or optional excipient to prevent or limit the dissolution of the composition already deposited within the lumen during the injections after the initial injection.

In some cases, the lumen of the strut tube is not entirely filled with the composition even after multiple cycles of injecting the injection solution.

The composition remaining in the lumen after one or more cycles of injecting an injection solution and changing the condition of pressure and temperature is the therapeutic agent or pharmaceutical formulation thereof, in a solid or a semi-solid form. In some embodiments, the semi-solid has a viscosity of not less than 15,000 cP, while in other embodiments, the viscosity may be not less than 10,000 cP. In still other embodiments, the composition remaining in the lumen after the solvent has evaporated is a fluid having a viscosity not less than 10 cp, preferably not less 100 cP, more preferably not less than 500 cP, even more preferably not less than 1000 cP, and still even more preferably, not less than 5000 cP. In some embodiments, the therapeutic agent is dispersed, either uniformly or non-uniformly, in the excipient.

In other embodiments, the material injected may be a composition that is a semi-solid or high viscosity fluid. The composition may be a pharmaceutical formulation of a therapeutic agent and an excipient that may be non-volatile, and may possess characteristics such that it is a semi-solid or liquid at about 20° C. to about 30° C. and a pressure of about one atmosphere. The pharmaceutical formulation may have a viscosity of not more than 10,000 cP when the pharmaceutical formulation is at a temperature of about 20° C. to 30° C. and a pressure of about one atmosphere, and may be referred to as a "high viscosity pharmaceutical formulation." In some embodiments, the viscosity of the pharmaceutical formulation may be at least 10 cP or at least 100 cP, and in other embodiments, at least 1000 cP at a temperature of about 20° C. to 30° C. and a pressure of about one atmosphere. In still further embodiments, the pharmaceutical formulations may have a viscosity of at least 5000 cP or at least 7500 cP at a temperature of about 20° C. to 30° C. and a pressure of about one atmosphere. The viscosity of the pharmaceutical formulation may be high enough that the pharmaceutical formulation does not leak, or flow, or essentially does not leak or flow, through the side openings and/or end openings in the strut tube prior to the stent formed of such strut tubes being implanted. As a result, the viscosity of the fluid may be decreased as the size of the side openings is decreased.

These embodiments differ from the other embodiments in that neither a solvent, nor heating, of the composition is required. Therefore, the composition injected, which is a high viscosity pharmaceutical formulation, is free of, or essentially free of, solvents. The pharmaceutical formulation may be in the form of a paste, a gel, or a hydrogel. A gel may be a semi-rigid material which is a colloidal dispersion of a solid in a liquid. For a hydrogel, the liquid is water.

The therapeutic agent may be formulated with a high viscosity, non-volatile (or essentially non-volatile) excipient such that the resulting pharmaceutical formulation has a viscosity of at least 10 cP. The excipients used may have a viscosity of at least 10 cP, but preferably at least 100 cP, and more preferably at least 250 cP, at a temperature of about 20° C. to 30° C. and a pressure of about one atmosphere. In some embodiments, the excipient has a viscosity of at least 1000 cP or at least 5000 cP at a temperature of about 20° C. to 30° C. and a pressure of about one atmosphere. In some embodiments, the excipient is a semi-solid. In some embodiments, the excipients used may have a viscosity of slightly less than 100 cP, such as for example, at least 85 cP, at a temperature of about 20° C. to 30° C. and a pressure of about one atmosphere, but when formulated the viscosity of the pharmaceutical formulation may be at least 100 cP.

The excipients chosen may be non-volatile, or essentially non-volatile. Non-volatile may be a vapor pressure of not more than 0.6 ton at 20° C. to 30° C. when measured at a pressure of about one atmosphere. In some embodiments, the excipient may have a vapor pressure of not more than 0.06 ton at 20° C. to 30° C. when measured at a pressure of about one atmosphere. In some embodiments, the excipient may lose not more than 3% of the initial weight when left in an open vial at USP controlled room temperature for 24 months, while in other embodiments the excipient may lose not more than 1.5% of its' initial weight.

Examples of excipients that may be used to form a high viscosity pharmaceutical formulation include, without limitation, triglycerides, diglycerides, monoglycerides, soybean oil, safflower oil, peanut oil, vegetable oil, fatty alcohols, liquid poloxamers, TWEEN™ 20 (polysorbate 20), TWEEN™ 80 (polysorbate 80), poly(ethylene glycol) of a number average molecular weight of less than or equal to 1000 Daltons and/or about 1000 Daltons, propylene glycol, glycerol, benzyl benzoate, benzyl alcohol, dimethyl sulfoxide, N-methylpyrrolidone, and any combination thereof.

The therapeutic agents used include, without limitation, any one or any combination of those listed previously.

The therapeutic agent may be dissolved in the excipient, dispersed in the excipient, or both dissolved and dispersed in the excipient. In some embodiments including the high viscosity formulation as well as the pharmaceutical formulations with a low melting excipient or pharmaceutical formulations using other excipients, the therapeutic agent may be in the form of and/or incorporated in microspheres, nanoparticles, microparticles, and/or microshells. A nanoparticle refers to a particle with a characteristic length (e.g., diameter) in the range of about 1 nm to about 1,000 nm. A micro-particle refers to a particle with a characteristic length in the range of greater than 1,000 nm and less than about 10 micrometers. A plurality of particles is characterized by a distribution of particle size, and in some embodiments, the plurality of particles has an average diameter, as determined by dynamic light scattering, in the range of 0.1 nm to 1,000 nm, or to about 1,000 nm, while in other embodiments, the plurality of particles has an average diameter greater than 1,000 nm and less than 10 micrometers, or about 10 micrometers. The polydispersity of the plurality of particles, as measured by the ratio of the D90 to the D10 of the particle size distribution determined by dynamic light scattering may be not more than 10, not more than 8, not more than 6, or preferably, not more than 4.

Particles such as microspheres and nanoparticles typically include a therapeutic agent and another material. However, in some embodiments the particles may be neat therapeutic agent, that is the particles may be, for example and without limitation, 100% or about 100% therapeutic agent, at least 99.0% therapeutic agent, at least 99.5% therapeutic agent, at least 99.8% therapeutic agent, or essentially 100% therapeutic agent. In other embodiments, the particles may have therapeutic agents mixed, dispersed, and/or dissolved, and/or otherwise incorporated in the particle material. The particle material can be biostable, biodegradable, or a combination thereof, and it may also be polymeric, metallic, ceramic, glass, or any combination thereof. In a preferred embodiment, the particles may include a polymer and a therapeutic agent, and may optionally an excipient.

Particles with therapeutic agent distributed throughout the particle material may be referred to as matrix type or monolithic type drug delivery particles. The therapeutic agent may be homogeneously, or substantially homogeneously, distributed throughout the matrix of particle material, or the therapeutic agent distribution may be non-uniform. The particles can also encapsulate a therapeutic agent having an outer shell of material with an inner core containing the therapeutic agent, and optionally another excipient. Such particles with an outer shell without therapeutic agent are typically referred to as reservoir type particles. In other embodiments, the therapeutic agent may be included in an exterior coating or shell of the particle surrounding a core. Particles may also be any combinations of the above.

The therapeutic agent may be included in a micelle, vesicle or liposome which may be dispersed in the excipient. A "micelle" refers to an aggregate (or cluster) of surfactant molecules. "Surfactants" refer to chemicals that are amphiphilic, which means that they contain both hydrophobic and hydrophilic groups. Micelles tend to form when the concentration of surfactant is greater than a critical micelle concentration, and is essentially an aggregation of the molecules essentially forming a sphere with the hydrophilic group of the surfactant molecules forming a shell that contacts water around the hydrophobic groups in the core. Micelles may be formed from, for example, block copolymers and/or lipids. Therapeutic agent may partition into the core or be incorporated within the micelle. A vesicle is a relatively small and enclosed compartment or shell formed by at least one lipid bilayer. A lipid bilayer if formed from phospholipid molecules having a hydrophilic head and a hydrophobic tail. Two layers of molecules form a shell in which the hydrophobic tails form the middle "layer" of the shell with the hydrophilic head groups facing the exterior of the vesicle and the interior aqueous compartment. In some embodiments, the exterior shell may be cross-linked to stabilize the vesicle or micelle.

The high viscosity pharmaceutical formulation may include the therapeutic agent in the form of any type of particles listed above, or any combination of types of the particles listed above.

The high viscosity pharmaceutical formulation may include between 2 wt % and 90 wt %, about 2 wt %, or about 90 wt % therapeutic agent, preferably between 5 wt % and 50 wt %, about 5 wt %, or about 50 wt % therapeutic agent, or more preferably, between 10 wt % and 35 wt %, about 10 wt %, or about 35 wt % therapeutic agent whether the therapeutic agent is dispersed in an excipient directly or in the form of a particle. If the pharmaceutical formulation includes microspheres, nanoparticles, microparticles, microshells, micelles, vesicles, liposomes and/or another type of particle (collectively "particles"), the weight percent of the pharmaceutical formulation that is particles may be between 2 wt % and 90 wt %, about 2 wt %, or about 90 wt % particles, preferably between 5 wt % and 50 wt %, about 5 wt %, or about 50 wt % particles, or more preferably, between 10 wt % and 35 wt %, about 10 wt %, or about 35 wt % particles. The particles may be between about 2 wt % and about 100%, or in some embodiments 100% therapeutic agent. If the particles include another material in addition to the therapeutic agent, the particles may be between 5 wt % and 95 wt % therapeutic agent, about 5 wt %, or about 95 wt %, preferably between 20 wt % and 95 wt %, about 20 wt %, or about 95 wt % therapeutic agent.

For the high viscosity pharmaceutical formulation, or any pharmaceutical formulation that includes particles, whether the particles are of essentially neat therapeutic agent, and/or the particles include a particle material in addition to the therapeutic agent, the ratio of the internal diameter of the lumen of the strut tube, or other structural element, to the average diameter of the particles may be not more than 10, preferably not more than 12, more preferably not more than 15, and even more preferably not more than 20. In some embodiments, the ratio of the internal diameter of the lumen of the structural element, such as a strut tube, to the D90 of the plurality of particles may be not more than 10, preferably not more than 12, more preferably not more than 15, and even more preferably no more than 20. It is believed that use of particle diameters that are a larger fraction of the internal lumen diameter may result in poor flow of the pharmaceutical formulation, and/or uneven distribution of the therapeutic agent throughout the lumen.

The pharmaceutical formulation may include other excipients in addition to the high viscosity excipient such as, without limitation, stabilizers, anti-oxidants, lubricants, carriers, and/or diluents. If the therapeutic agent is dispersed in the excipient and/or particles including therapeutic agent are dispersed in the excipient, the pharmaceutical formulation may also include surfactants or dispersants to minimize and/or prevent aggregation of the particles in the pharmaceutical formulation.

The injection of the high viscosity pharmaceutical formulation uses a pressure in the range of 10 to 20,000 lb/in$^2$ gauge. Other embodiments encompass a pressure in the range of 10 to 5,000 lb/in$^2$, 10 to 15,000 lb/in$^2$, 10 to 10,000 lb/in$^2$, 100 to 10,000 lb/in$^2$, 10,000 to 15,000 lb/in$^2$, 12,000 to 15,000 lb/in$^2$, or 15,000 to 20,000 lb/in$^2$. Unless expressly stated otherwise, all injection pressures refer to gauge pressure.

In some embodiments, the injection may occur in an inert atmosphere and/or in a low humidity atmosphere as described previously.

In some embodiments, the high viscosity pharmaceutical formulation utilizes some heating. The pharmaceutical formulation may be heated to a specific temperature or to within a specific temperature range prior to injection. In some embodiments, the specific temperature, or the lower end of the specific temperature range to which the pharmaceutical formulation is heated prior to injection, may be at, about, or at least 28° C., 30° C., 35° C., or 40° C. The upper temperature of the range may be at or about 30° C., 35° C., 40° C., or 45° C. Also, during the injection and optionally for some time after the completion of the injection, the strut tube, the injector, and the pharmaceutical formulation within the lumen and/or within the injector may be maintained at a specific temperature, and/or within a specific temperature range which may be the same as or different from the specific temperature or the specific temperature range to which the pharmaceutical formulation is heated prior to injection. In some embodiments, the specific temperature, or the lower end of the specific temperature range at which the pharmaceutical formulation is maintained during the injection, may be at, about or at least 28° C., about or at least 30° C., about or at least 35° C., or about or at least 40° C. The upper temperature of the range may be at or about 30° C., at or about 35° C., at or about 40° C., or at or about 45° C. The temperature may fluctuate within a temperature range or around a specified temperature.

In some embodiments, the strut tube, the injector, and the pharmaceutical formulation within the lumen of the strut tube and/or injector may be maintained at a temperature, or within a temperature range, sufficient to maintain the viscosity of the pharmaceutical formulation of not more than 10,000 cP during the injection, preferably not more than 5,000 cP during the injection, more preferably, not more than 1,000 cP during the injection, and even more preferably, not more than 100 cP.

For those embodiments utilizing heating of the high viscosity pharmaceutical formulation, the temperature of the pharmaceutical formulation may not exceed a temperature, which may be referred to as a maximum temperature, at which significant degradation of the therapeutic agent would occur during the time period of the heating prior to the injection, during the injection, and optionally for some time period after the injection. In some embodiments, a maximum temperature may be selected such that the degradation of the therapeutic agent is not more than 3%, and in still other embodiments, not more than 1% during the time period of the heating prior to the injection, during the injection, and optionally for some time period after the injection. Various embodiments of the invention encompass a maximum temperature of 60° C., 65° C., 70° C., and 80° C.

In any of the embodiments utilizing a pharmaceutical formulation, if the excipients are expected to also diffuse from or be released from the lumen of the strut tube and into the body upon implantation, the molecular weight of an excipient may be chosen such that the excipient can be excreted from the body via the kidneys if the excipient is not an excipient which biodegrades in the body into fragments which can be excreted from the body via the kidneys. In some embodiments, one or more of the excipients, or all of the excipients, or all biostable excipients, may have a number average molecular weight of less than 40,000 Daltons, preferably less than 35,000 Daltons, and more preferably, less than 30,000 Daltons.

In some embodiments, material may be injected into the strut tube after side openings are formed in the tube. While the material is being injected into the tube, it may be desirable to cover and seal off the side openings, that is mask the side openings, to prevent leakage of the material. If the side openings are not sealed, or masked, during the injection process, the material injected into one end of the tube may not reach or flow to the opposite end of the tube. Masking or sealing the side openings helps to minimize waste of the material, and helps to ensure that the tube is filled completely and that the material is uniformly distributed throughout the tube. If the side openings are formed on the abluminal surface of the stent, the side openings can be sealed by wrapping or encasing the abluminal surface with a thin sheet or thin tube of elastic material, which can be pressurized or shrunk down onto the stent, such as, for example, by heat shrinking. If the side openings are formed on the luminal surface of the stent, the side openings can be sealed by wrapping or encasing the luminal surface with a thin sheet or thin tube of elastic material in the form of a balloon or a bladder that can be pressurized or inflated inside the tubular scaffolding of the stent.

Figure 4A:
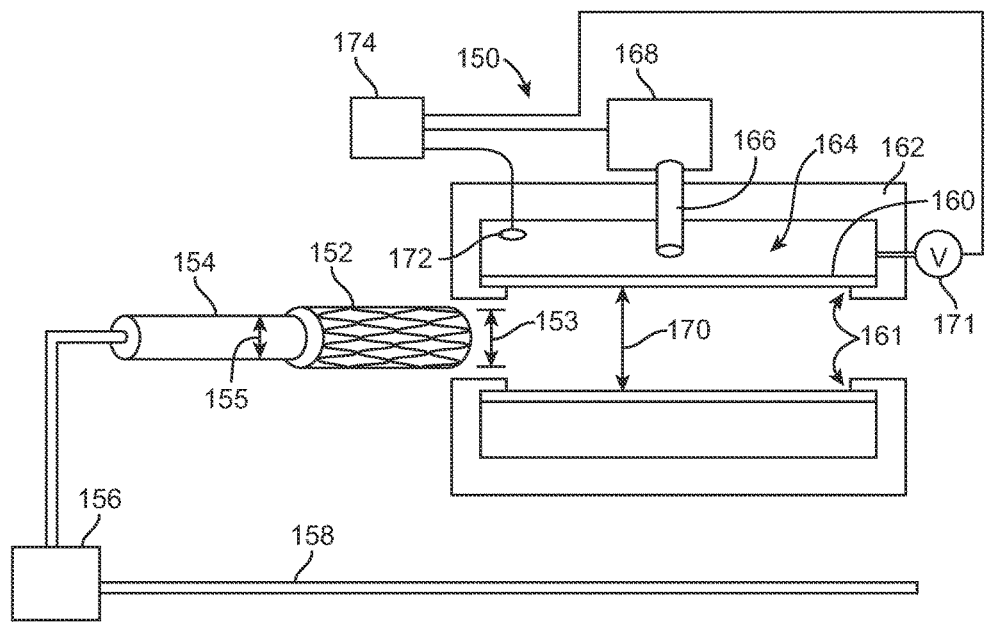
FIGS. 4A and 4B depict a device for sealing openings in hollow struts of a stent.
Figure 4B:
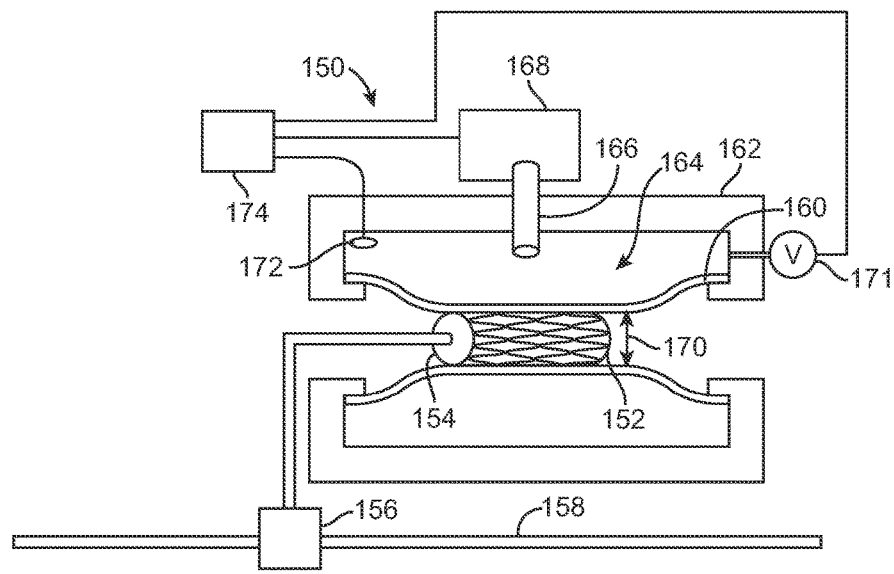

In FIGS. 4A and 4B a device 150 is shown for sealing side openings during an injection process. In FIG. 4A, a stent 152 is shown adjacent a cylindrical support 154 sized to fit within the tubular scaffolding of the stent. The cylindrical support 154 is attached to a gear system or motor 156 for moving the cylindrical support axially along a rail 158. When the stent 152 is mounted on the cylindrical support 154, activation of the motor 156 allows the stent to be moved automatically in and out of the device 150.

The device 150 includes an elastic cover sleeve 160 and a manifold 162 that together form a fluid filled plenum chamber 164. The elastic cover sleeve 160 is in the shape of a cylindrical tube and has circular openings at opposite ends of the sleeve. The opposite ends of the sleeve 160 are fixedly connected to the manifold 162. The connection 161 between the cover sleeve 160 and the manifold 162 is fluid tight. The plenum chamber 164 is annular in shape and encircles the elastic cover sleeve 160. The plenum chamber 164 can be filled with a gas or a liquid. The manifold includes a port hole 166 to allow movement of fluid into and out of the plenum chamber 164. The elastic cover sleeve 160 has an inner diameter 170 and is configured to move from a first orientation as shown in FIG. 4A to a second orientation as shown in FIG. 4B. The inner diameter 170 is greater when the elastic cover sleeve is in the first orientation than when in the second orientation. The elastic cover sleeve 160 is configured to move between the first orientation and the second orientation according to a change in fluid pressure inside the plenum chamber. The fluid pressure inside the plenum chamber 164 can be adjusted by a fluid pump 168 connected to the port hole 166.

When the elastic cover sleeve 160 is in the first orientation, as shown in FIG. 4A, the inner diameter 170 is greater than the outer diameter 155 of the cylindrical support 154 and the outer diameter 153 of the tubular scaffolding of the stent 152 so as to allow the stent to be moved into and out of the elastic cover sleeve 160 without making contact with the elastic cover sleeve 160. When the elastic cover sleeve 160 is in the second orientation, the inner diameter 170 is substantially the same as or is less than the outer diameter 155 of the cylindrical support 154 and the outer diameter 153 of the tubular scaffolding of the stent 152. In FIG. 4B, the inner diameter 170 of the elastic cover sleeve 160 presses against the stent 152 and is prevented in part from becoming smaller by the presence of the stent 152 and cylindrical support 154 within the elastic cover sleeve 160.

In use, the stent 152 is placed inside the elastic cover sleeve 160 while in the first orientation. Next, fluid pressure inside the plenum chamber 164 is adjusted in such a way to cause or allow the elastic cover sleeve 160 to move toward the second orientation until the elastic cover sleeve presses against the abluminal surface of the stent and seals the side openings on the abluminal surface, as shown in FIG. 4B. The cylindrical support 154 prevents the tubular scaffolding of the stent from being crimped down to a smaller diameter by the pressure applied by the elastic cover sleeve 160. An injector, such as shown in FIG. 2 or other device, is coupled to a stent strut (i.e., tube) such as shown in any one of FIGS. 3A-3D. While the elastic cover sleeve 160 presses against the abluminal surface of the stent 152, the material is forced into the stent struts by the injector. Next, fluid pressure inside the plenum chamber 164 is adjusted in such a way to cause or allow the elastic cover sleeve 160 to move to the first orientation to allow removal of the stent from the device 150.

In some embodiments, the inner diameter 170 of the elastic cover sleeve 160 is greater than the outer diameter 155 of the cylindrical support 154 and the outer diameter 153 of tubular stent scaffold when the elastic cover 160 is an undeformed or natural state. When installed in the manifold 162, the elastic cover sleeve 160 is configured to reduce its inner diameter 170 (i.e., move from the first orientation to the second orientation) with an increase of fluid pressure inside the plenum chamber 164. For example, while the stent 152 is inside the elastic cover sleeve 160, the fluid pump 168 can be activated by an electronic controller 174 to force fluid into the plenum chamber 164 and thereby cause the elastic cover sleeve 160 to move from the first orientation (FIG. 4A) toward the second orientation and press against the abluminal surface of the stent (FIG. 4B). After the material has been injected into the struts of the stent, the fluid pump 168 or a release valve 171 is activated to allow fluid to exit the plenum chamber 164, which allows the elastic cover sleeve 160 to self-expand to the first orientation. Thereafter, the stent 152 can be removed from the device 150.

In other embodiments, the inner diameter 170 of the elastic cover sleeve 160 is less than the outer diameter 153 of tubular stent scaffold when the elastic cover 160 is an undeformed or natural state. When installed in the manifold 162, the elastic cover sleeve 160 is configured to increase its inner diameter 170 (i.e., move from the second orientation to the first orientation) with a decrease of fluid pressure inside the plenum chamber 154. For example, while the stent 152 is outside the elastic cover sleeve 160, the fluid pump 168 can vacuum fluid out of the plenum chamber 164 to cause the elastic cover sleeve 160 to move to the first orientation (FIG. 4A). Next, the stent 152 is placed into the elastic cover sleeve 160, then the fluid pump 168 or the release valve 171 is activated to allow fluid to return into the plenum chamber 164, which allows the elastic cover sleeve 160 to self-contract toward the second orientation and press against the abluminal surface of the stent (FIG. 4B). After the material has been injected into the struts of the stent, the fluid pump 168 is again activated to vacuum fluid out of the plenum chamber 164 and cause the elastic cover sleeve 160 to move to the first orientation (FIG. 4A). Thereafter, the stent 152 can be removed from the device 150.

Referring again to FIGS. 4A and 4B, there is a pressure sensor 172 inside the plenum chamber 164 configured to detect fluid pressure inside the plenum chamber. The electronic controller 174 is in communication with the pressure sensor 172 and the fluid pump 168. The electronic controller 174 includes electrical circuits and may include a combination of electronic components, such as transistors, memory devices, programmable logic controllers, microcontrollers and/or microprocessors. The controller 174 is configured to activate the fluid pump 168 based at least on an input signal from the pressure sensor 172. For example, the controller 174 can be configured to activate the fluid pump 168 so as to maintain a predetermined fluid pressure inside the plenum chamber 164 while the stent 152 is inside the elastic cover sleeve 160. The predetermined fluid pressure can correspond to a desired pressure that is applied by the elastic cover sleeve 160 on the stent 152 to prevent damage to the stent or prevent the stent from being crimped to a smaller diameter.

In either the case of an external elastic cover sleeve to cover abluminal side openings or a balloon or bladder to cover the luminal side openings, the elastic cover sleeve, balloon, or bladder may be made from an elastomeric material that has sufficient mechanical strength to withstand the pressure of the composition within the lumen that passes out through the side openings as well as any external pressure applied on to the elastomeric material to conform its shape to that of the stent. Examples of such materials include, without limitation: silicone; various types of polyurethane; styrene-isobutylene styrene triblock polymers; thermoplastic polyester elastomers such as HYTREL®, a trade name of DuPont, some examples of which are poly (ether urea urethanes), poly(ester urethanes), poly(carbonate urethanes) poly(tetramethylene glycol-co-butanediol-co-toluene diisocyanate), poly(dimethyl siloxane); thermoplastic elastomer nylon copolymer such as PEBAX®, which is a trade name of Arkema Group for polyether block amide thermoplastic elastomers, some examples of which are copolymers of nylon-12 and poly(tetramethylene glycol) and copolymers of poly(ethylene glycol) and nylon-6. Another possible material that may be used for either the balloon or the sleeve is heat shrink tubing such as cross-linked polyethylene. The material of the balloon and/or the sleeve may not absorb a significant quantity of the therapeutic agent and/or optional excipient. If the material injected is an injection solution which includes a solvent, the elastomeric material may not swell to any appreciable extent in the solvent. In some embodiments, the extent of swelling by any one of or any combination of the solvent, the therapeutic agent, and the optional excipient may be less than 10% by weight, preferably less than 2% by weight, and even more preferably, less than 1% by weight.

In FIGS. 5A-5C a device 180 is shown to prevent the material being filled into strut tubes during an injection process from escaping out through side openings 181 formed into the strut tubes. In FIG. 5A, a stent 182 is shown carried on a cylindrical support 184 sized to fit within the tubular scaffolding of the stent. The entire stent 182 is disposed within the pressure chamber 190 throughout the injection process. The cylindrical support 184 is attached to a gear system or motor 186 for moving the cylindrical support axially along a rail 188, the direction of movement being parallel to the longitudinal, central axis 189 of the stent. When the stent 182 is mounted on the cylindrical support 184, activation of the motor 186 allows the stent to be moved automatically within the pressure chamber 190. Movement of the stent within the pressure chamber alters the surrounding fluid pressure experienced by the stent, as will be explained below. The pressure chamber 190 has a conical shape such that its curved inner surface 191 is tapered and reduces in diameter between opposite ends of the chamber. The pressure chamber 190 has a relatively narrow end 192 and a relatively wide end 194.

In other embodiments, the pressure chamber 190 is cylindrical such that its curved inner surface 191 is not tapered and has a uniform diameter between opposite ends of the pressure chamber.

As shown in FIG. 5B the exemplary pressure chamber 190 has a circular cross-section. The stent 182 and the cylindrical support 184 are radially centered within the curved inner surface 191 of the pressure chamber. A gap that serves as a gas flow path 196 exists radially between the stent 182 and the curved inner surface 191. The gas flow path 196 completely encircles the stent 182. The gas flow path 196 has a substantially annular shape in radial cross-section as shown in FIG. 5B. The annular shape is bounded by the outer surface 185 of the cylindrical support 184 and the curved inner surface 191 of the pressure chamber 190. The gas flow path 196 has a radial cross-sectional area that increases from the narrow end 192 to the wide end 194 of the pressure chamber 190.

A gas supply or pump 198 is connected by a conduit to the narrow end 192 of the pressure chamber 190. The gas pump 198 is configured to force gas through the conduit and into the pressure chamber 190 when the gas pump is activated. The gas forced into the pressure chamber 190 exits at the opposite end of the pressure chamber through a gas outlet 199 at the wide end 194.

In the illustrated embodiment, the entire stent 182 is formed of a continuous, coiled tube 183. Various segments of the coiled tube 183 serve as stent struts that are connected end to end to collectively form the stent scaffolding for supporting biological tissue after implantation within a patient. The opposite ends of the coiled tube 183 have tube openings. The tube opening closest the narrow end 192 of the pressure chamber 190 is connected to an injector 200. The injector 200 is configured to force the material into the coiled tube 183 when the injector 200 is activated. The tube opening closest the wide end 194 of the pressure chamber 190 is connected to a gas conduit 201 that leads to the exterior of the pressure chamber 190. The gas conduit 201 allows fluid pressure at the tube opening of the coiled tube 183 closest the wide end 194 to equalize with ambient pressure outside the pressure chamber 190.

The injector 200 and the gas conduit 201 can be connected to the coiled tube 183 in various ways shown in FIGS. 3A-3D or by other methods. The injector 102 in FIGS. 3A-3D would be replaced by the injector 200 or the gas conduit 201. The injector 200, cylindrical support 184, and the gas conduit 201 pass through fluid-tight seals in apertures formed through walls of the pressure chamber 190.

There are a plurality of side openings 181 on the abluminal surface of the stent. The side openings 181 are spaced apart from each other and are distributed along the entire longitudinal length of the stent 182. The side openings 181 extend into and provide access to the lumen of the coiled tube 183 of the stent. The side openings 181 allow a composition that is filled into the coiled tube 183 to diffuse or disperse out at a later time, such as after the stent is implanted within a patient.

The coiled tube 183 initially contains only gas at the start of the injection process. When the injector 200 is activated, the material is forced into the stent 182 through the tube opening closest the narrow end 192, which creates an internal fluid pressure gradient within the coiled tube 183. The internal pressure gradient corresponds to a relatively high fluid pressure within the tube opening attached to the injector 200 and a relatively low fluid pressure at the tube opening attached to the gas conduit 201.

It will be appreciated that the material may begin to spill out of the side openings 181 during the injection process. To inhibit or prevent the material from spilling out of the side openings 181, an external fluid pressure gradient is created outside of the coiled tube 183 by gas flow through the pressure chamber 190. The words "internal" and "external" when used to modify the phrase "pressure gradient" refer to fluid pressure gradients that exist inside and outside the coiled tube 183, respectively.

As gas is forced into the narrow end 192 of the pressure chamber 190, the gas flows longitudinally from the narrow end 192 to the wide end 194 where it exits the pressure chamber 190. The fluid pressure in various longitudinal locations (along the x-axis shown in FIG. 5A) within the pressure chamber 190 (and external to the coiled tube 183) depends at least in part on resistance to gas flow at the respective location, and resistance to gas flow depends at least in part on the radial cross-sectional area of the gas flow path 196 at the respective location. The gas flow creates the external fluid pressure gradient in a longitudinal direction due to the decreasing resistance to gas flow arising from the increase in the cross-sectional area of the gas flow path 196 from the narrow end 192 to the wide end 194. The fluid pressure surrounding the stent will be greater at longitudinal locations near the narrow end 192 than at longitudinal locations near the wide end 194. Preferably, the external pressure gradient substantially matches the internal pressure gradient so that at any particular longitudinal location intersecting the stent 182, the fluid pressure inside the coiled tube 183 is substantially equal to the fluid pressure outside the coiled tube. The composition is inhibited or prevented from spilling out of the side openings when, during the injection process, the pressure inside the coiled tube 138 and the pressure outside the coiled tube are substantially equal to each other.

A first set of pressure sensors 202 are longitudinally distributed and spaced apart from each other and disposed within the pressure chamber 190 to provide a measurement of the external pressure gradient. The pressure sensors 190 may be coupled to the cylindrical support 184 so that they move with the stent 183. Another set of pressure sensors 203 are disposed on the injector 200 and the gas conduit 201 to provide a measurement of the internal pressure gradient. Both sets of pressure sensors 202, 203, the injector 200, the gas pump 198, and the motor 186 are in communication with an electronic controller 204, which includes electrical circuits and may include a combination of electronic components, such as transistors, memory devices, programmable logic controllers, microcontrollers and/or microprocessors. The controller 204 is configured to simultaneously activate the gas pump 198, the injector 200, and/or the motor 186 based at least on an input signal from one or both sets of pressure sensors 202, 203 so that internal and external pressure gradients substantially match each other. For example, the internal and external pressure gradients may be matched by having the controller 204 reduce or increase the flow of gas from the gas pump 198, reduce or increase the flow of the composition into the coiled tube 183, and/or move the stent 182 longitudinally within the pressure chamber 190.

The internal pressure gradient (i.e., the pressure gradient that exist inside the coiled tube 183) may not be static during the injection process. That is, the pressure gradient profile may change in shape and/or value as the material is injected into and moves through the coiled tube 183. For example, FIGS. 5D and 5E, depict the internal and external pressure gradients as curves Pi and Pe, respectively, as a function of longitudinal position X within the coiled tube 183. FIG. 5D depicts the internal and external pressure gradients when the stent is at the position shown in FIG. 5A and material 207 is just starting to be injected into the coiled tube 183 at location X1. FIG. 5D depicts the internal and external pressure gradients at a later time, when the stent is at the position shown in FIG. 5C and the material 207 has reached location X2 within the coiled tube 183. The internal and external pressure gradients Pi and Pe have shifted upwards in FIG. 5D, indicating a rise in pressure from FIG. 5C.

To keep the external pressure gradient Pe (i.e., the pressure gradient that exists outside the coiled tube 183) matched with the internal pressure gradient Pi, the controller 204 may, as the material moves through the coiled tube 183, reduce or increase the flow of gas from the gas pump 198, reduce or increase the flow of the material into the coiled tube 183, and/or move the stent 182 longitudinally within the pressure chamber 190. For example and not limitation, in cases where the internal pressure gradient increases during the injection process, the controller 204 may cause the stent 182 to longitudinally move in accordance with input from one or both sets of pressure sensors 202, 203. Simultaneously while the material is injected into the coiled tube opening 205 closest the narrow end 192, the longitudinal stent movement can be from a first position close to the wide end 194 of the pressure chamber 190 (such as shown in FIG. 5A) to a second position close the narrow end 192 of the pressure chamber (such as shown in FIG. 5B). The above described method of injecting material into opening 205 and moving the stent toward the narrow end 192 of the chamber 190 corresponds to Case 1 in TABLE 1.

TABLE 1

|  | Injector connected to Stent | Travel Direction of Material Injected into Stent | Travel Direction of Stent while Material is Injected |
| --- | --- | --- | --- |
| Case 1 | At Opening 205 | From Opening 205 to Opening 206 | From FIG. 5A to FIG. 5C |
| Case 2 | At Opening 205 | From Opening 205 to Opening 206 | From FIG. 5C to FIG. 5A |
| Case 3 | At Opening 206 | From Opening 206 to Opening 205 | From FIG. 5A to FIG. 5C |
| Case 4 | At Opening 206 | From Opening 206 to Opening 205 | From FIG. 5C to FIG. 5A |

In other embodiments, the injection process proceeds according to Case 2 in TABLE 1. Simultaneously while the material is injected into the coiled tube opening 205 closest the narrow end 192, the longitudinal stent movement can be from a first position close to the narrow end 192 of the pressure chamber 190 (such as shown in FIG. 5C) to a second position close the wide end 194 of the pressure chamber (such as shown in FIG. 5A).

In other embodiments, the injection process proceeds according to Case 3 in TABLE 1. The injector 200 is connected to the coiled tube opening 206 closest the wide end 194 (instead of being connected to the coiled tube opening 205 closest the narrow end 192, as shown in FIGS. 5A and 5B). Simultaneously while the material is injected into the coiled tube opening 206 closest the wide end 194, the longitudinal stent movement can be from a first position close to the wide end 194 of the pressure chamber 190 (such as shown in FIG. 5A) to a second position close the narrow end 192 of the pressure chamber (such as shown in FIG. 5C).

In other embodiments, the injection process proceeds according to Case 4 in TABLE 1. The injector 200 is connected to the coiled tube opening 206 closest the wide end 194. Simultaneously while the material is injected into the coiled tube opening 206 closest the wide end 194, the longitudinal stent movement can be from a first position close to the narrow end 192 of the pressure chamber 190 (such as shown in FIG. 5C) to a second position close the wide end 194 of the pressure chamber (such as shown in FIG. 5A).

In the illustrated embodiment, the pressure chamber 190 has a frustoconical shape. The particular shape of the curved inner surface 191 is selected to provide a desired pressure gradient longitudinally across the chamber. It will be appreciated that shapes for the curved inner surface 191 other than what is illustrated herein may be implemented to provide a desired pressure gradient. In alternative embodiments, for example, the longitudinal cross-sectional profile of the curved inner surface 191 may be concave or convex instead of the straight cross-sectional profile shown in FIGS. 5A and 5C. In some embodiments, the longitudinal cross-sectional profile of the curved inner surface 191 can have abrupt changes in diameter so as to produce steps or notches instead of the continuous and gradual change in diameter shown in FIGS. 5A and 5C.

In another embodiment, the masking or sealing of the side openings may be accomplished by applying a thin layer of a water soluble and/or bio-absorbable coating over the strut tube or the stent. The coating would bridge or cover the holes, and optionally may fill the holes. Therefore the coating would not be a conformal coating over the entire outer surface of the strut tube, but would conform to the outer surface except for the side openings, which may be bridged or webbed over, and optionally may be completely or partially filled. The coating would remain on the stent in effect masking or sealing the side openings until implanted at which time it would dissolve, or degrade. Thus, the coating would prevent and/or limit the leakage of the material during injection and would also prevent or limit leaking of the composition filling the lumen of the strut tubes during storage of the device. In some embodiments, the side openings may be plugged, or filled, either partially, completely, or essentially completely, with a bioabsorable material to prevent or limit the leakage of material during injection, and to prevent or to limit the leakage of the composition during storage. In some embodiments, at least 95 wt %, at least 98 wt %, or at least 99 wt % of the composition remains within the lumen of the strut tube at the end of a storage time period. The storage time period may be 6 months, 12 months, 18 months, or 24 months. Materials useful for the thin water soluble and/or bioabsorable coating include, without limitation, poly(ethylene oxide), poly(ethylene glycol), PLURONIC® polymers, poly(vinyl pyrrolidone), gelatin, poly(2-hydroxyethyl methylmethacrylate), dextrose, dextran, poly(vinyl alcohol), poly(glycolide), poly (D,L-lactide-co-glycolide), poly(L-lactide-co-glycolide), poly(caprolactone-co-glycolide), poly(anhydrides), and poly(orthoesters).

In some embodiments, a water soluble and/or bio-absorbable coating is applied over the strut tube or the stent prior to the loading of a composition into the lumen of the strut tube, and in such embodiments, the viscosity of the composition filling the lumen of the strut tube may be lower than without a coating as the coating may prevent the leakage of the composition from the side openings during storage and during loading. In those embodiments in which a water soluble and/or bio-absorbable coating is applied to the strut tube prior to loading, the viscosity of the composition filling the strut tube at a temperature of approximately 20° C. to 25° C. and one atmosphere may be below 100 cP such as from about 1 cP to about 5 cP, about 5 cP to about 10 cP, about 5 cP to about 20 cP, about 10 cP to about 50 cP, about 20 cP to about 80 cP, about 50 cP to about 100 cP, or greater than 100 cP. In other embodiments, the viscosity at a temperature of approximately 20° C. to 25° C. and one atmosphere may be about 10 cP to about 1000 cP. In some of the embodiments in which the coating is applied prior to loading, the composition may have a viscosity of not less than 100 cP, not less than 200 cP, or not less than 1000 cP. In those embodiments using a water soluble and/or bio-absorbable coating, the composition that is loaded into the lumen of a strut tube, the extent of swelling by any one of or any combination of the solvent, the therapeutic agent, and the optional excipient may be less than 10% by weight, preferably less than 2% by weight, and even more preferably, less than 1% by weight where the % swelling is determined after 3 months storage at a temperature of 25° C. or an equivalent thereof. In some embodiments, the excipient and/or therapeutic agent may not migrate into the coating to an appreciable extent (a mass increase of the coating of more than about 10%), while in other embodiments, the excipient and/or therapeutic agent may migrate into the coating.

Embodiments of the present invention encompass injection of an injection solution as well as injection of a composition such as, for example, those described above.

A composition may be loaded into a strut tube in a number of other ways, as an alternative to pushing or displacing material into a strut tube. For example, pressure outside or inside the strut tube can be decreased to draw gas out of the strut tube and draw material into the strut tube. In some embodiments, material may be injected into one opening using a pressure greater than that of the surrounding environment and at the same time a vacuum may be applied at another opening to assist in filling the lumen. Thus, for any of the above injection methods, alternative embodiments exist in which the material may be drawn into the lumen via a decrease in pressure, such as for example, by applying a vacuum, and other embodiments encompass methods using both injection and application of a vacuum.

Figure 6:
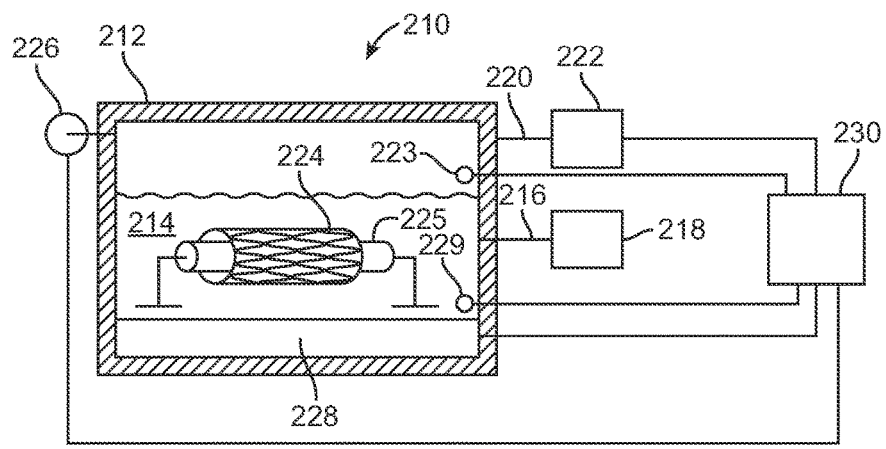
FIG. 6 depicts a system for filling the interior of a stent with hollow struts.

In FIG. 6, fluid pressure outside the strut tube is decreased to a level below fluid pressure inside the strut tube. Material can be drawn into the strut tube through an opening at the end of the strut tube, through side openings in the tube, or through both end openings and side openings. An apparatus 210 for loading material into a stent structure comprises a vacuum chamber 212 that contains a material 214 that is supplied to the vacuum chamber by a first conduit 216 connected to a reservoir 218 or other source of additional material. A second conduit 220 connects the vacuum chamber 212 to a pump 222 configured to reduce pressure inside the vacuum chamber when the pump is activated. A pressure sensor 223 inside the vacuum chamber 212 is configured to detect pressure inside the vacuum chamber. An electronic controller 230 is in communication with the pressure sensor 223 and the pump 222, and is configured to activate the pump based at least on an input signal from the pressure sensor. The electronic controller 230 includes electrical circuits and may include a combination of electronic components, such as transistors, memory devices, programmable logic controllers, microcontrollers and/or microprocessors.

A stent 224 is disposed inside vacuum chamber 212. An exemplary stent comprises a tubular scaffolding formed from a plurality of strut tubes formed from a continuous tube into which the material 214 is to be loaded. The strut tubes have at least one opening immersed in the material 214. In the illustrated embodiment, the entire stent 224 is immersed in the material 214 such as may be desired when a plurality of side openings have been formed throughout the stent. The stent 224 is supported by a cylindrical support 225 for transporting the stent into and out of the vacuum chamber 212. Internal dimensions of the vacuum chamber are sized to accommodate the cylindrical support 225. The cylindrical support 225 is sized to fit within the central lumen of the tubular scaffolding of the stent 224 and is configured to keep the stent immersed in the material 214 in the vacuum chamber 212.

Initially, the strut tubes of the stent 224 are gas-filled. When the stent is immersed into the material 214, the material 214 may not enter all parts of the strut tubes due to gas entrapped inside the strut tubes, viscous resistance, and capillary forces. Before the pump 222 is activated, the fluid pressure inside the strut tubes is substantially the same as the fluid pressure inside the vacuum chamber 212. Next, the pump 222 is activated so that gas inside the vacuum chamber 212 is drawn out of the vacuum chamber, which makes the pressure inside the vacuum chamber and fluid surrounding the strut tubes lower than pressure inside the strut tubes. The difference in pressure causes the previously entrapped gas to exit the strut tubes thereby allowing the material 214 to fill the strut tubes. After the strut tubes are filled with the material 214, the pump 222 or a valve 226 is activated to allow gas to flow back into the vacuum chamber 212 and thereby allow the fluid pressure inside the vacuum chamber 212 to equalize with ambient pressure. The valve 226 is coupled to a vent formed into the wall of the pressure chamber 212. In some instances, after a vacuum is applied, the strut tubes are evacuated and have essentially a vacuum inside them. Then, when the pressure of chamber 212 is equalized with ambient pressure, such as by opening of the valve 226, the material 214 is driven into the strut tubes. This process may be repeated if necessary to effect complete loading of material 214 into the strut tubes. Thereafter, the stent 224 is removed from the vacuum chamber 212.

Still referring to FIG. 6, the apparatus 210 also includes a temperature control device 228 configured to cool down or lower the temperature of the material 214 inside the vacuum chamber 212, as may be desired when the material includes a volatile liquid. A temperature sensor 229 inside the vacuum chamber is configured to detect temperature of the material 214. The controller 230 is in communication with the temperature sensor 229 and the temperature control device 228, and is configured to activate a cooling element in the temperature control device, based at least on an input signal from the temperature sensor, so that the temperature control device 228 cools the material inside the vacuum chamber 212. The controller 230 can activate the cooling element to keep any volatile liquid in the material 214 from boiling when pressure inside the vacuum chamber is being reduced by the pump 222. In this embodiment, the temperature control device 228 functions as a cooling device.

In other embodiments, the controller 230 is configured to activate a heating element in the temperature control device 228, based at least on an input signal from the temperature sensor, so that the temperature control device 228 heats the material inside the vacuum chamber 212. The controller 230 can activate the heating element in order to reduce the viscosity of the material in the vacuum chamber and to make it easier for the material to flow into the opening to the lumen. In this embodiment, the temperature control device 228 functions as a heating device.

Figure 7:
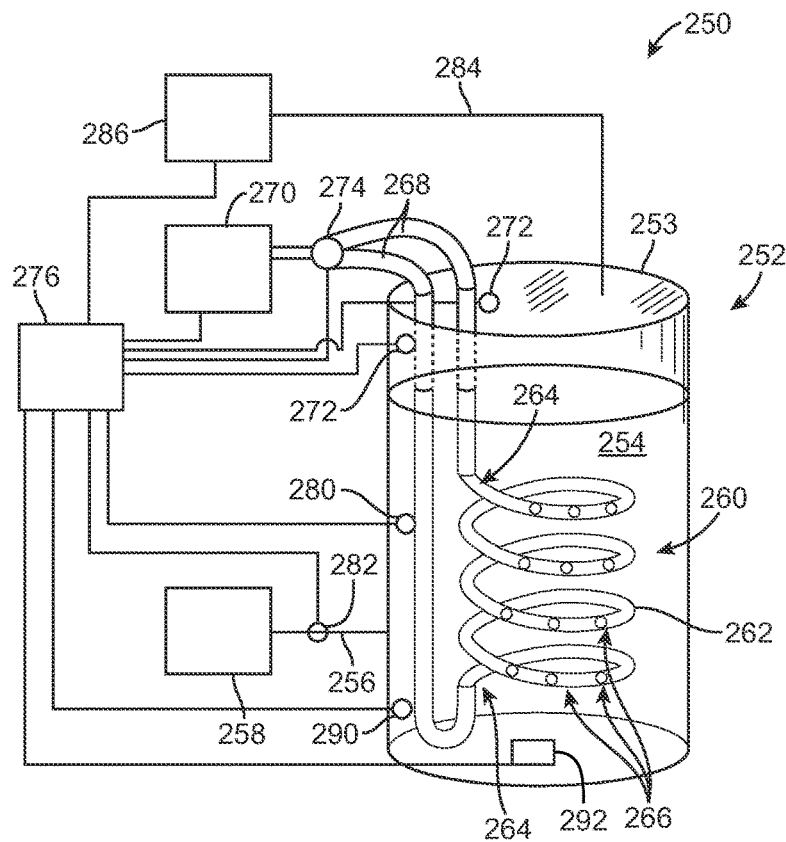
FIG. 7 depicts another system for filling the interior of a stent with hollow struts.

Another embodiment is illustrated in FIG. 7. In FIG. 7, fluid pressure inside the strut tubes is decreased to a level below fluid pressure outside the strut tubes. Material is drawn into the strut tubes through side openings in the tube. An apparatus 250 for loading material into a stent structure comprises container 252 of material 254 that is supplied to the container by a supply conduit 256 connected to a reservoir 258 or other source of additional material. The container 252 has a removable lid 253. Internal dimensions of the container 252 are sized to allow placement of a stent 260 inside the container. In the illustrated embodiment, the entire stent 260 is formed of a continuous, coiled tube 262. Various segments of the coiled tube 262 serve as stent struts that are connected end to end to collectively form the stent scaffolding for supporting biological tissue after implantation within a patient. The ends 264 of the coiled tube 262 are shown immersed in the material 254 but need not be immersed in order to fill the coiled tube with the material. There are openings at opposite ends 264 of the coiled tube 262. Two gas conduits 268 connect the tube openings at the opposite ends 264 of the coiled tube 262 to a suction pump 270 configured to suction gas when the pump is activated. The gas conduits 268 can be connected to the coiled tube 262 in various ways shown in FIGS. 3A-3D or by other methods. The injector 102 in FIGS. 3A-3D would be replaced by the gas conduits 268.

There are a plurality of side openings 266 (holes and/or pores) spaced apart along the length of the coiled tube 262. The side openings 266 are immersed in the material 254 to allow material 254 to fill the coiled tube 262.

Initially, the coiled tube 262 of the stent 260 is gas-filled. The stent 260 is connected to the gas conduits 268 and immersed into the material 254. The material 254 may not enter all parts of the coiled tube 262 due to gas entrapped inside the coiled tube. Before the suction pump 270 is activated, the pressure inside the coiled tube is substantially the same as the pressure inside the container 252. Next, the suction pump 270 is activated by an electronic controller 276 so that gas inside the coiled tube 262 is drawn out, which makes the fluid pressure inside the coiled tube lower than the fluid pressure of the fluid 254 surrounding the coiled tube. Drawing out the previously entrapped gas through the gas conduits 268 causes the material 254 to be drawn into the side openings 266 and thereby fill the coiled tube.

After the coiled tube is filled with the material 254, material 254 will begin to be drawn into the gas conduits 268. There are sensors 272 disposed on the gas conduits 268 for detecting the presence of material 254 inside the gas conduits 268. There is also a valve 274 which connects the gas conduits 268 to the suction pump 270. The electronic controller 276 is in communication with the suction pump 270, the sensors 272, and the valve 274. The electronic controller 276 includes electrical circuits and may include a combination of electronic components, such as transistors, memory devices, programmable logic controllers, microcontrollers and/or microprocessors. The controller 276 is configured control the suction pump 270 and the valve 274 based at least on an input signal from the sensors 272. For example, when only one of the sensors 272 detects the presence of material 254 inside one of the gas conduits 268, the controller 276 activates the valve 274 so as to stop suction in the material-filled gas conduit while still allowing suction to continue in the other gas conduit. After the coiled tube 262 is completely filled, as indicated by the presence of material 254 inside both gas conduits 268, the coiled tube 262 is removed from the container 262 and disconnected from the gas conduits 268.

The filling process can include actively lowering the fluid pressure inside the coiled tube 262, as already described above, while simultaneously increasing the fluid pressure of the material 254 surrounding the coiled tube 262, as will be described below.

There is a pressure sensor 280 inside the container 252 configured detect fluid pressure of the material 254. There is a supply pump 282 along the supply conduit 256 configured to force the material 254 into the container 252 when the supply pump is activated. The controller 276 is configured control the supply pump 282 based at least on an input signal from the pressure sensor 280. For example, the controller 276 can be configured to activate the suction pump 270 while simultaneously activating the supply pump 282, thereby increasing the difference in fluid pressure between inside and outside of the coiled tube 262. The supply pump 282 is controlled in such a way by the controller 276 so that a predetermined fluid pressure of the material 254 is maintained during the filling process.

There is a gas supply conduit 284 connecting the container 252 to a gas supply pump 286 configured to force gas into the container when the gas supply pump is activated. The controller 276 is configured control the gas supply pump 286 based at least on an input signal from the pressure sensor 280. For example, the controller 276 can be configured to activate the suction pump 270 while simultaneously activating the gas supply pump 286, thereby increasing the difference in fluid pressure between inside and outside of the coiled tube 262. The gas supply pump 286 is controlled in such a way by the controller 276 so that a predetermined fluid pressure of the material 254 is maintained during the filling process.

There is optionally a temperature sensor 290, such as and without limitation a thermocouple or resistance temperature detector, inside the container 252 configured to detect the temperature of the material 254. There is a heating and/or cooling element 292, such as for example and without limitation, a coil through which a heating fluid or a cooling fluid may flow, inside the container 252 configured to heat or cool the material 254. The controller 276 is configured control the heating or cooling element 292 based at least on an input signal from the temperature sensor 290.

In alternative embodiments, the container 252 can be an open or closed container without any means for controlling the pressure of the material 254. In such embodiments, the apparatus 260 includes no supply pump 282 and no gas supply pump 286.

In alternative embodiments, the stent 260 is carried on a cylindrical support that transports the stent down into and up out of the container 252. Such a cylindrical support is configured to keep the stent immersed in the material 254. Such a cylindrical support is connected to a gear arrangement or a motor which is coupled to a rail. Such a cylindrical support can be configured in the same manner as the cylindrical support 154 of FIGS. 4A and 4B.

In alternative embodiments, the sensors 272 are configured to detect the presence of gas bubbles in the gas conduits 268. The suction pump 270 is controlled by the controller 276 so that the suction pump 270 draws the material carried by the container 252 into the side openings 266 to the lumen and into the gas conduits 268. The controller 276 causes the suction pump 270 to continue drawing the material until gas bubbles cease to pass from the lumen of the stent 260 and into the gas conduits 268. The absence of gas bubbles can indicate that the lumen of the stent 260 is completely filled with the material. The controller 276 can be configured to stop the suction pump 270 based at least on an indication from the sensors 272 of the absence of air bubbles. Optionally, the suction pump 270 can be a positive displacement pump, such as a gear pump, which is configured to draw the material from the gas conduits 268 (having passed through the lumen of the stent 260) and return the material back into the container 252.

For those embodiments in which the stent is immersed in material, after it has been loaded with the material, the stent may be removed from the material and any material or components thereof adhering to the outer surface of the stent may be removed. The methods of removal include, for example and without limitation, wiping the exterior with a cloth, brushing, wiping, blowing, rinsing, application of a high DC voltage, or centrifuging the material or components therefore from the outer surface of the stent, or any combination thereof. The removal is accomplished without or with minimal removal (for example, without limitation, less than 5 wt %) of the composition within the lumens of the strut tubes of the stent. If the material is at a temperature above about 20° C., the removal may occur prior to, after, and/or simultaneous with cooling of the stent and its contents. If the material is an injection solution, the removal may occur before, after, and/or simultaneous with the alteration of the condition of temperature and pressure. As a non-limiting example, the stent may be removed from the solution, and the condition of temperature and pressure changed resulting in the deposition of a composition including a therapeutic agent into the lumen and potentially also onto the outer surface of the stent. The stent may then be rinsed with a solvent which may be the same as or different from the solvent of the injection solution, or the stent may be wiped to remove the composition adhering to the exterior of the stent.

The material that may be pushed or drawn into the lumen of the structural element for any of the above described apparatuses (e.g. FIGS. 4, 5, 6, and 7) may be any of the compositions described above for use in the injection methods or the material may be an injection solution as described above. In some embodiments, the material may be a therapeutic agent that has been melted. In other embodiments, the material may be a pharmaceutical formulation including a therapeutic agent and an excipient such as for example a low melting excipient, as described above. In still other embodiments, the material may be a high viscosity pharmaceutical formulation. For either of the first two scenarios, that is the molten therapeutic agent or pharmaceutical formulation with a low melting excipient, the material 254 in the container 252 may be heated to a temperature, or within a temperature range, sufficient to maintain the material in a fluid state. For the high viscosity pharmaceutical formulation, the material may be optionally heated. In some embodiments, if the material 254 is a high viscosity pharmaceutical formulation, the material 254 is heated to a specific temperature to maintain the viscosity at or below a specified viscosity, for example and without limitation, 100 cP at a pressure of one atmosphere pressure. For any of compositions discussed above, the material 254 in the container 252 may be heated to a specific temperature and maintained at or above the specific temperature, where the specific temperature may be at or about 30° C., at or about 35° C., at or about 40° C., at or about 45° C., or higher. For the composition which is either a molten therapeutic agent or a pharmaceutical formulation including a therapeutic agent and a low melting excipient, the specific temperature may be the melting temperature of the therapeutic agent, the melting temperature of the pharmaceutical formulation, or the melting temperature of the excipient, or higher, and in still other embodiments the specific temperature may be 5° C., 10° C., or 15° C. higher than the melting temperature of the therapeutic agent, the pharmaceutical formulation, or the excipient. For the case in which the material is any of the above compositions, the temperature used may be one that avoids, or limits, significant degradation of the therapeutic agent, or limits the degradation to not more than 3 wt % or not more than 1 wt %.

If the material is heated, the stent, filled with a composition as described above, may be cooled to a temperature of approximately 20° C. to 25° C. and one atmosphere as previously described, after removal from the container 252.

If the material is a high viscosity pharmaceutical formulation, the size of the therapeutic agent particles, if the therapeutic agent is dispersed in the excipient, and/or if the therapeutic agent is added as a particle, may be such that the particles do not plug the side openings upon filling the lumen.

In other embodiments the material 254 in the container 252 may be an injection solution as described previously, that is a composition including a therapeutic agent, and optionally an excipient, dissolved and/or dispersed in a solvent. As for the injection solution described previously, the solvent used may be one that is in a gas phase at about 20° C. to 25° C. and one atmosphere, and therefore, readily evaporates. The container 252 and the material 254 may be maintained at a condition of temperature and pressure such that the material, which is an injection solution, remains in a liquid or supercritical state. Once the lumen of the stent structure is filled with the injection solution and the stent has been removed from the container, the condition of the stent may be altered or changed such that the stent and composition therein is at about 20° C. to about 25° C. and one atmosphere. Under such a condition the solvent readily evaporates leaving the composition within the lumen of the strut tubes of the stent.

If the material 254 in container 252 is an injection solution, to fill the lumen with a desired quantity of the composition, there may be a need to subject the stent to more than one cycle of immersion in the material, removal from the material, and alteration of the condition of pressure and temperature. The cycle may, optionally, also include an operation to remove the composition and/or solvent from the outer surface of the stent. In subsequent immersion cycles, it is potentially possible for the composition that has already been deposited in the lumen to be re-dissolved into the injection solution. To limit or prevent this occurrence, the injection solution may be near or at the saturation limit of the therapeutic agent and/or the optional excipient.

In any of the above embodiments, one or more openings, for example and without limitation, an opening at end 264 as shown in FIG. 7, may be temporarily plugged before immersion into the material or immediately after removal from the material. If the material is an injection solution, one or both openings, if more than one opening is present, at the end of the tube may be plugged soon after removal from the solution, followed by the change in the condition of temperature and pressure, and then followed by removal of the plugs after the solvent has evaporated or has substantially evaporated.

As with the methods involving injection, any of the immersion methods discussed above may be performed in an inert atmosphere and/or low humidity atmosphere as described previously.

Figure 8A:
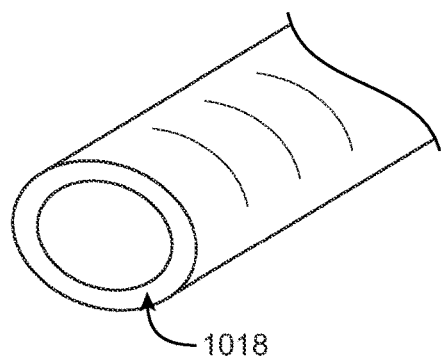
FIGS. 8A and 8B depict the end view of an open tube, and the end view of a tube that has been crimped.
Figure 8B:
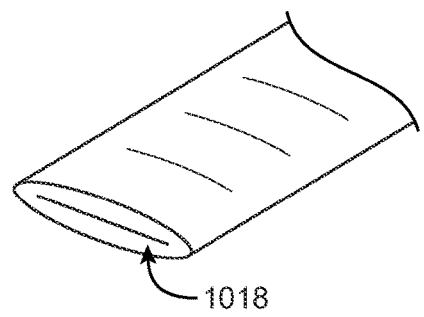

Once the strut tube is filled with a composition by any of the methods described above, the opening(s), for example and without limitation the inlet openings at the ends of the tube, may be sealed. The ends may be sealed by mechanical sealing the ends. A mechanical seal involves crimping or compressing the ends down to seal, or essentially seal, the opening. FIGS. 8A and 8B illustrate the end view of an opening at the end of a strut tube, and a sealed end. As shown in FIGS. 8A and 8B, the edge 1018 of the tube may be circular or approximately circular in shape before crimping as shown in FIG. 8A, and after crimping, may be essentially a linear or rectangular shape as shown in FIG. 8B. The ends may be crimped together, welded together, or both crimped and welded. The end may be sealed by welding it to an adjacent strut tube.

Figure 9A:
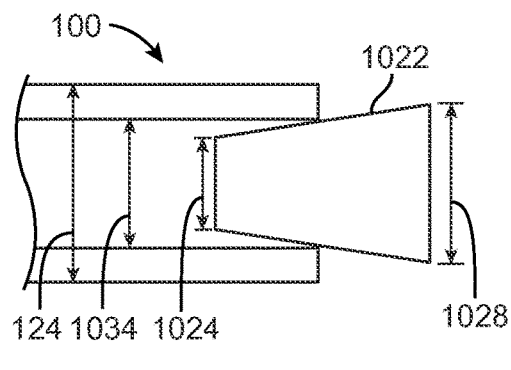
FIGS. 9A, 9B, and 9C depict two exemplary plugs and an exemplary cap.
Figure 9B:
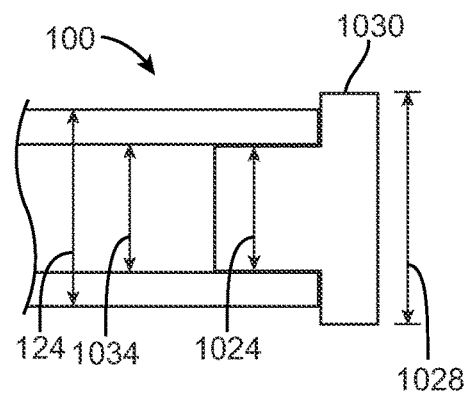
Figure 9C:
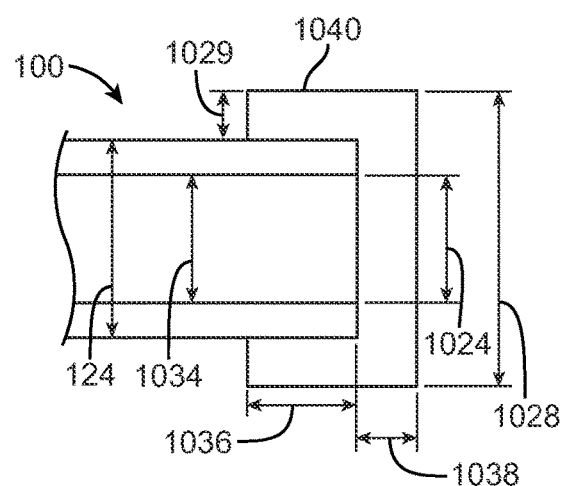

Alternatively, the ends may be plugged or capped. A plug may be an object which is designed to fit into a hole tightly, and generally prevents liquid or fluid from passing through the hole. FIGS. 9A and 9B are exemplary and non-limiting examples of plugs 1022 and 1030, respectively, and FIG. 9C is an exemplary embodiment of a cap 1040 for an open end of a tube 100. Plugs 1022 and 1030 each have a smaller diameter, 1024, and a larger diameter 1028. For plug 1022 which is essentially the shape of a truncated cone, the smaller diameter 1024 is less than that of the diameter of the lumen of the tube 1034, and the larger diameter 1028 is greater than that of the lumen of the tube, and may be greater than the outer diameter 124 of tube 100. For plug 1030, the smaller diameter 1024 is equal to, slightly less than, or slightly greater than the inner diameter of the lumen of the tube 1034 and the larger diameter of the plug 1028 is sufficiently greater than the smaller diameter 1024 to prevent the plug from being pushed entirely into the lumen. Plug 1030 has the shape of two concentrically stacked cylinders in which the cylinder with the larger diameter 1028 has a height/diameter ratio <1, preferably <0.5, and even more preferably, <0.25. The cylinder of the smaller diameter 1024 has a height/diameter ratio that is at least 0.25, preferably 0.5 or greater, and which may be 1 or more.

The cap 1040 is in the shape of essentially a cylinder having a cylindrical hole concentrically counter bored in the center. The cap 1040 also has a smaller diameter 1024 which is equal to, or slightly smaller than the outer diameter 124 of the tube. The cap may stay on the end of the tube by compression fitting. The length of the side 1036 of the cap should be sufficient to keep cap on the end of the tube, and the ratio of the side 1036 to the thickness of the top 1038 may be 1.5 or more. The larger diameter 1028 of cap 1040 is a function of the smaller diameter 1024 and the wall thickness 1029 of sides of the cap.

A plug may be placed in the end of the tube preventing material, such as a composition, from flowing out of the end. The plugs or caps may be temporary or intended to remain on during implantation, that is essentially permanent. The plug or cap may be polymeric, metallic, ceramic, glass, another material, or any combination thereof. In preferred embodiments, the plug or cap is made from, that is entirely, polymeric, or it consists essentially of, a polymer. In the various embodiments, the polymer may be a water soluble polymer, a biostable polymer, a biodegradable polymer, or a combination thereof. If a biostable polymer is used for the plug or cap, the polymer may be relatively impermeable to the therapeutic agent and optional excipient. As used herein, "relatively impermeable" with respect to the properties of the biostable polymer plug or cap may be a weight gain of less than 5% over the course of 24 months in storage under controlled room temperature as defined by the USP, or may be a plug, that if used to seal one or more openings in a stent that has been filled with a composition, retains, at least 95 wt % of the initial composition weight the stent after 24 months in storage under controlled room temperature as defined by the USP. In some embodiments, plugs or caps may be selected such that when used to seal one or more openings in a stent that has been filled with a composition, retains, at least 97 wt %, or at least 98%, of the initial composition weight after 24 months in storage under USP controlled room temperature.

With respect to the embodiments of the present invention, the term "plugged" will be used but embodiments also encompass having the ends "capped."

In some embodiments, at least one opening, such as, for example and without limitation, an inlet opening at an end of the tube, may be plugged or capped prior to the injection of a material. Similarly, if the end is plugged prior to injecting the injection solution, the plug or cap, whether including a biostable polymer, a biodegradable polymer, or both, and/or other materials, may not more 10% by weight, preferably not more than 5% by weight, and even more preferably, not more than 1% by weight solvent and/or the composition of a therapeutic agent and an optional excipient, over the course of the injection, and optionally for some time period after the injection. For a biodegradable plug or cap, weight gain after implantation may occur as a result of water absorption by the plug or cap.

In some embodiments, the both ends of the tube are sealed and the injection or immersion may occur primarily through the side openings. In such embodiments, only some of the sidewall openings may be masked while others are used for injection and still others are left open to allow air to escape and/or a vacuum may be applied.

Once the strut tubes of a stent have been filled with a composition and some openings optionally sealed, the outer surface, or at least a portion of the outer surface of, a stent having hollow struts may be coated. The coating may be polymeric, metallic, glass, ceramic, other material, or any combination thereof. In preferred embodiments, the coating includes a polymer. A typical coating process involves dissolving and/or dispersing the coating materials, such as, for example, a polymer, optionally with other excipients and/or a therapeutic agent, in a solvent to form a coating solution, and disposing the coating solution over the outer surface of the stent by procedures such as spraying, brushing, wiping or directly depositing the solution onto the surface of the stent. The solution may be applied by immersing the stent in the solution. Non-limiting examples of other processes of applying a coating, which may or may not include a solvent, are plasma deposition processes, electrostatic deposition processes, and other dry powder application processes. Such coating procedures are well-known in the art. Any coating process may be executed in such a manner as to prevent or limit to a minimal amount (for example, not more than 5 wt %) removal of the composition within the lumens of the strut tubes.

The coating may comprise a polymer, a therapeutic agent, and/or other materials. If a therapeutic agent is included in the coating, the therapeutic agent may be the same as, or different from, the therapeutic agent of the composition in the lumens of the strut tubes. In some embodiments, the therapeutic agent of the composition within the strut tubes may differ from the therapeutic agent in the coating only in that it the one is a salt, hydrate, or polymorph of the other, or the two are different salts or hydrates of the same chemical entity. In other embodiments the therapeutic agent in the composition of the strut tubes may be different chemical entities, that is the chemical entity having the pharmacological activity is different.

In preferred embodiments, the coating comprises a polymer, which may be a biostable polymer, a biodegradable polymer, or a combination thereof. The coating may comprise a primer layer free of, or essentially free of, therapeutic agents. The coating may also include other excipients. Non-limiting examples of such excipients include lubricating agents, fillers, plasticizing agents, surfactants, diluents, mold release agents, agents which act as therapeutic active agent carriers, binders, anti-tack agents, anti-foaming agents, viscosity modifiers, anti-oxidants, stabilizers, potentially residual levels of solvents, and potentially any other agent which aids in, or may be desirable in, the processing of the material, and/or may be useful or desirable as a component of the final product. Surfactants may be used for the preparation of a dispersion of polymer and/or therapeutic agent in a solvent or fluid.

Embodiments of the present invention encompass coatings in which the coating layer, or materials included in the coating layer such as a polymer and/or therapeutic agents, are not covalently bound or chemically bound to the surface to which the coating is applied (the substrate surface, or a previously applied coating layer). Embodiments also encompass stents with a coating formed by the application of one or more layers as described above, and includes stent with coatings in which one or more materials migrate from one layer to another either during the coating application process and/or after the coating application process has been completed.

Examples of polymers that may be used in the various embodiments of the present invention include, without limitation, poly(N-acetylglucosamine) (chitin); chitosan; poly (hydroxyvalerate); poly(hydroxybutyrate), poly(hydroxybutyrate-co-valerate); poly(3-hydroxybutyrate); poly(4-hydroxybutyrate); poly(3-hydroxyvalerate); poly (hydroxybutyrate-co-valerate); polyorthoesters; polyanhydrides; homopolymers of any of the following and random and block copolymers of any combination of the following: D-lactic acid, L-lactic acid, DL-lactic acid, mesolactide, caprolactone (including but not limited to, ε-caprolactone), glycolide (glycolic acid), trimethylene carbonate, valeroactone, γ-undecalactone, β-methyl-δ-valerolactone, and hydroxycarboxylic acids (including, but not limited to, 3-hydroxybutyric acid, 4-hydroxybutyric acid, 3-hydroxyvaleric acid, 4-hydroxyvaleric acid, 5-hydroxyvaleric acid, dimethylglycolic acid, β-hydroxypropanic acid, α-hydroxybutyric acid, α-hydroxycaproic acid, β-hydroxycaproic acid, γ-hydroxycaproic acid, δ-hydroxycaproic acid, δ-hydroxymethylcaproic acid, ε-hydroxycaproic acid, and ε-hydroxymethylcaproic acid); poly(glycolide-co-caprolactone) polymers; poly(thioesters); polyethylene amide; polyester amide polymers; polyethylene acrylate; acrylate and methacrylate polymers; co-poly(ether-esters) (e.g., PEO/PLA); polyphosphazenes; biomolecules (e.g., fibrin, fibrinogen, cellulose, starch, collagen and hyaluronic acid); polyurethanes; silicones; polyesters; polyolefins; polyisobutylene and ethylene-alphaolefin copolymers; acrylic polymers; vinyl halide polymers and copolymers (e.g., polyvinyl chloride); polyvinyl ethers (e.g., polyvinyl methyl ether); polyvinylidene halides (e.g., polyvinylidene chloride); polyacrylonitrile; polyvinyl ketones; polyvinyl aromatics (e.g., polystyrene); polyvinyl esters (e.g., polyvinyl acetate); acrylonitrile-styrene copolymers; ABS resins; polyamides (e.g., Nylon 66 and polycaprolactam); polycarbonates; polyoxymethylenes; polyimides; polyethers; rayon; rayon-triacetate; cellulose and derivatives thereof and copolymers thereof (including without limitation cellulose acetate, cellulose butyrate, cellulose acetate butyrate, cellophane, cellulose nitrate, cellulose propionate, cellulose ethers, and carboxymethyl cellulose); and any copolymers and any blends of the aforementioned polymers.

Additional representative examples of polymers for use in the various embodiments of the present invention include, without limitation, ethylene vinyl alcohol copolymer (commonly known by the generic name EVOH or by the trade name EVAL™); poly(butyl methacrylate); poly(vinylidene fluoride-co-hexafluoropropylene) (e.g., SOLEF® 21508, available from Solvay Solexis PVDF of Thorofare, N.J.); polyvinylidene fluoride (otherwise known as KYNAR™, available from Atofina Chemicals of Philadelphia, Pa.); poly(tetrafluoroethylene-co-hexafluoropropylene-co-vinylidene fluoride); ethylene-vinyl acetate copolymers; and polyethylene glycol; and copolymers and combinations thereof.

As used herein, the terms poly(D,L-lactide) (PDLL), poly(L-lactide) (PLL), poly(D,L-lactide-co-glycolide) (PDLLG), and poly(L-lactide-co-glycolide) (PLLG) are used interchangeably with the terms poly(D,L-lactic acid) (PDLLA), poly(L-lactic acid) (PLLA), poly(D,L-lactic acid-co-glycolic acid) (PDLLAGA), and poly(L-lactic acid-co-glycolic acid) (PLLAGA), respectively.

Any of the above polymers or materials specifically listed may be used individually and/or in combination with any other polymer and/or materials listed herein. Likewise, therapeutic agents may be combined or used individually.

Various embodiments of the current invention encompass both uncross-linked and cross-linked polymers, branched and unbranched polymers, and dendritic polymers. In preferred embodiments, the polymers used may be uncross-linked or not crosslinked.

EXAMPLES

The following examples are given to aid in understanding the invention, but it is to be understood that the invention is not limited to the particular materials, apparatus, or procedures of the examples.

Example 1

Prospective Example

An 18 mm in length stent with hollow struts is fabricated from a biocompatible metal such as stainless steel. PEG 1000 having a number-average molecular weight of about 1000 Daltons is melted at a temperature at or above 45° C. Zotarolimus is dissolved into the PEG 1000 forming a composition of 90% by weight PEG 1000 and 10% by weight zotarolimus. The stent is pre-heated to a temperature of about 45° C., and maintained at 45° C. or slightly higher while the composition, which is also maintained at 45° C. or a higher temperature, is injected into the lumen of the struts. A sufficient volume to provide 180 ug of zotarolimus is injected. If the volume of the strut lumens is not sufficient to obtain 180 ug of zotarolimus at a weight ratio of PEG 1000 to zotarolimus of 9:1, the weight ratio may be adjusted slightly such that the stent contains 180 ug of zotarolimus.

Example 2

Prospective Example

Dexamethasone acetate, with a melting temperature of 240° C., is melted to form a composition which is injected into the lumen of a 12 mm stent having hollow struts. The injector is coupled to an inlet opening of the tube forming the stent until the composition is visible at the other end of the tube. The filled stent is cooled to about 20° C. to 25° C. The dexamethasone acetate solidifies.

Example 3

Prospective Example

The stent from example 2, after being loaded with dexamethasone acetate, is coated by spray coating. The coating is obtained by spraying a 1:1 weight ratio blend of zotarolimus and poly(glycolide-co-D,L-lactide), of a 75:25 molar ratio of the constituent monomers glycolide:D,L lactide, in acetone onto the outer surface of the stent such that 120 ug of zotarolimus is contained in the resulting coating on the stent. When the stent is implanted, the zotarolimus is first released to control smooth muscle cell proliferation. After about 1 to 3 months, the stent begins to release dexamethasone acetate which is released over an extended period of time providing an anti-inflammatory effect.

Example 4

Prospective Example

A composition is obtained by dissolving zotarolimus in the solvent HFC-134a™ ($CF_3CFH_2$) at a weight ratio of 1:2 zotarolimus to solvent. By maintaining the temperature less than −30° C. or the pressure at or above 40 psi, the composition is in a liquid state. An 18 mm stent with hollow struts is injected with the composition while maintaining either the pressure at or above 40 psi (gauge) and/or the temperature less than −30° C. so that the composition remains in a liquid state during the injection. After the stent is loaded or filled with the composition, the pressure is altered to about one atmosphere (~14.7 psi absolute). As a result of the pressure change, the solvent evaporates and escapes through the holes and/or openings in the stent. As a result 180 ug of zotarolimus is deposited within the lumen of the stent struts and there is no residual solvent, or a very low quantity of residual solvent due to the high vapor pressure of the solvent.

Example 5

Prospective Example

A composition is made by dissolving or dispersing zotarolimus in PEG 400, that is a poly(ethylene glycol) having a number-average molecular weight of about 400 and which is a liquid at a temperature of 25° C. and a pressure of one atmosphere. The composition formed is paste-like in consistency. About 300 ug of the paste is injected into a stent having hollow struts, specifically into the lumen of the hollow struts. The result is a stent containing 150 ug of zotarolimus.

Example 6

Prospective Example

A composition is made by dissolving zotarolimus in Capmul MCM EP, glycerol monocaprylocaprate (Abitec Corp Janesville, Wis.) at a weight ratio of 1/1. The composition forms a flowable, high viscosity fluid. An 18 mm stent with hollow struts is immersed in the composition. Application of vacuum, while heating at 45° C., followed by releasing the pressure to ambient fills the strut tubes with the composition. The result is a stent containing about 180 ug of zotarolimus.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention. Moreover, although individual aspects or features may have been presented with respect to one embodiment, a recitation of an aspect for one embodiment, or the recitation of an aspect in general, is intended to disclose its use in all embodiments in which that aspect or feature can be incorporated without undue experimentation. Also, embodiments of the present invention specifically encompass embodiments resulting from treating any dependent claim which follows as alternatively written in a multiple dependent form from all prior claims which possess all antecedents referenced in such dependent claim (e.g. each claim depending directly from claim 1 should be alternatively taken as depending from any previous claims).

What is claimed is:

1. An apparatus for loading material into a stent strut, the apparatus comprising:
   a pressure chamber;
   a stent support, wherein either one or both of the pressure chamber and the stent support are configured to translate, in a linear translation direction, relative to the other;
   a gas supply configured to move gas through the pressure chamber in the linear translation direction; and
   an injector configured to connect to a stent and deliver material into a hollow strut of the stent,
   wherein the pressure chamber comprises a narrow segment, a wide segment, and an internal space extending from the narrow segment to the wide segment, and wherein the stent support extends into the internal space, and the internal space has a cross-sectional area that increases from the narrow segment to the wide segment.

2. The apparatus of claim 1, further comprising a controller, wherein the stent support includes a contact point configured to contact a stent, and the controller is configured to linearly translate either one or both of the pressure chamber and the stent support such that a change occurs in a distance between the contact point and the wide segment of the pressure chamber.

3. The apparatus of claim 1, wherein the cross-sectional area includes a circular area and the stent support is radially centered in the circular area.

4. The apparatus of claim 1, wherein the gas supply is configured to move gas through the pressure chamber in a direction from the narrow segment to the wide segment of the pressure chamber.

5. The apparatus of claim 4, wherein the injector is configured to deliver material such that the material travels within the hollow strut in a direction from the narrow segment toward the wide segment of the pressure chamber.

6. The apparatus of claim 5, further comprising a controller, wherein stent support includes a contact point configured to contact a stent, and the controller is configured to translate either one or both of the pressure chamber and the stent support such that there is an increase in a distance between the contact point and the wide segment simultaneously while the injector delivers material.

7. The apparatus of claim 5, further comprising a controller, wherein stent support includes a contact point configured to contact a stent, and the controller is configured to translate either one or both of the pressure chamber and the stent support such that there is a decrease in a distance between the contact point and the wide segment simultaneously while the injector delivers material.

8. The apparatus of claim 4, wherein the injector is configured to deliver material such that the material travels from the wide segment toward the narrow segment of the pressure chamber.

9. The apparatus of claim 8, further comprising a controller, wherein stent support includes a contact point configured to contact a stent, and the controller is configured to translate either one or both of the pressure chamber and the stent support such that there is an increase in a distance between the contact point and the wide segment simultaneously while the injector delivers material.

10. The apparatus of claim 8, further comprising a controller, wherein stent support includes a contact point configured to contact a stent, and the controller is configured to translate either one or both of the pressure chamber and the stent support such that there is a decrease in a distance between the contact point and the wide segment simultaneously while the injector delivers material.

11. The apparatus of claim 1, further comprising at least one external pressure sensor coupled to the stent support, wherein the at least one external pressure sensor and the stent support maintain fixed positions relative to each other when either one or both of the pressure chamber and the stent support translate relative to the other, and the at least one external pressure sensor is configured to detect fluid pressure of gas flowing through the pressure chamber.

12. The apparatus of claim 11, further comprising a controller configured to control any one or a combination of the gas supply, the injector, and translation of the stent support, the control based at least on a signal from the at least one external pressure sensor.

13. The apparatus of claim 11, further comprising an internal pressure sensor configured to detect fluid pressure of material delivered out of the injector.

14. The apparatus of claim 13, further comprising a controller configured to control any one or a combination of the gas supply, the injector, and translation of the stent support, the control based at least on a signal from the at least one external pressure sensor and a signal from the internal pressure sensor.

15. The apparatus of claim 1, further comprising a stent on the stent support, the stent comprising stent struts formed from a tube, the tube having a lumen, an opening to the lumen, and a plurality of side openings to the lumen, wherein the injector is configured to deliver material through the opening and into the lumen.

* * * * *